United States Patent
Modak et al.

(10) Patent No.: US 9,968,101 B2
(45) Date of Patent: May 15, 2018

(54) BOTANICAL ANTIMICROBIAL COMPOSITIONS

(71) Applicant: The Trustees of Columbia University in the City of New York, New York, NY (US)

(72) Inventors: Shanta M. Modak, River Edge, NJ (US); Santoshkumar Dongre, New York, NY (US); Lauserpina Caraos, Hollis, NY (US); Nayana Baiju, Kochi (IN); Hari Krishnan Ramachandran, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days. days.

(21) Appl. No.: 14/267,606

(22) Filed: May 1, 2014

(65) Prior Publication Data
US 2014/0242198 A1    Aug. 28, 2014

Related U.S. Application Data

(63) Continuation of application No. PCT/US2012/037135, filed on May 9, 2012, which is
(Continued)

(51) Int. Cl.
| | |
|---|---|
| *A61K 36/15* | (2006.01) |
| *A01N 65/44* | (2009.01) |
| *A23L 3/3472* | (2006.01) |
| *A61K 36/752* | (2006.01) |
| *A61K 36/886* | (2006.01) |
| *A61K 36/31* | (2006.01) |
| *A61K 36/355* | (2006.01) |
| *A61K 36/899* | (2006.01) |
| *A61K 31/047* | (2006.01) |
| *A61K 31/045* | (2006.01) |
| *A61K 31/12* | (2006.01) |
| *A01N 31/04* | (2006.01) |
| *A01N 31/08* | (2006.01) |
| *A01N 37/36* | (2006.01) |
| *A01N 59/00* | (2006.01) |
| *A01N 59/16* | (2006.01) |
| *A01N 65/00* | (2009.01) |
| *A61K 8/34* | (2006.01) |
| *A61Q 17/00* | (2006.01) |
| *A61K 8/97* | (2017.01) |
| *A61K 36/00* | (2006.01) |
| *A61K 36/76* | (2006.01) |
| *A61K 36/81* | (2006.01) |
| *A61K 36/185* | (2006.01) |

(Continued)

(52) U.S. Cl.
CPC ............. *A01N 65/44* (2013.01); *A01N 31/04* (2013.01); *A01N 31/08* (2013.01); *A01N 37/36* (2013.01); *A01N 59/00* (2013.01); *A01N 59/16* (2013.01); *A01N 65/00* (2013.01); *A01N 65/22* (2013.01); *A23L 3/3472* (2013.01); *A61K 8/34* (2013.01); *A61K 8/922* (2013.01); *A61K 8/97* (2013.01); *A61K 31/045* (2013.01); *A61K 31/047* (2013.01); *A61K 31/12* (2013.01); *A61K 36/00* (2013.01); *A61K 36/15* (2013.01); *A61K 36/185* (2013.01); *A61K 36/28* (2013.01); *A61K 36/31* (2013.01); *A61K 36/355* (2013.01); *A61K 36/752* (2013.01); *A61K 36/76* (2013.01); *A61K 36/81* (2013.01); *A61K 36/886* (2013.01); *A61K 36/899* (2013.01); *A61Q 17/005* (2013.01); *A61Q 19/10* (2013.01)

(58) Field of Classification Search
None
See application file for complete search history.

(56) References Cited

U.S. PATENT DOCUMENTS

| | | | |
|---|---|---|---|
| 4,022,605 | A | 5/1977 | Konya et al. |
| 4,049,802 | A | 9/1977 | Fox, Jr. |

(Continued)

FOREIGN PATENT DOCUMENTS

| | | |
|---|---|---|
| CH | 654327 | 2/1986 |
| DE | 202004018623 U1 | 4/2005 |

(Continued)

OTHER PUBLICATIONS

U.S. Appl. No. 12/694,119 (US 2010/0172847), filed Jan. 26, 2010 (Jul. 8, 2010).
U.S. Appl. No. 12/016,788 (US 2009/0035228), filed Jan. 18, 2008 (Feb. 5, 2009).
U.S. Appl. No. 12/134,918 (US 2009/0004122), filed Jun. 6, 2008 (Jan. 1, 2009).
U.S. Appl. No. 12/367,851 (Abandoned), filed Feb. 9, 2009.
U.S. Appl. No. 12/694,141 (US 2010/0172848), filed Jan. 26, 2010 (Jul. 8, 2010).
U.S. Appl. No. 12/134,911 (US 2009/0029961), filed Jun. 6, 2008 (Jan. 29, 2009).
U.S. Appl. No. 12/136,530 (Abandoned), filed Jun. 10, 2008 (Dec. 18, 2008).
U.S. Appl. No. 13/335,363 (US 2012/0201902), filed Dec. 22, 2011 (Aug. 9, 2012).
U.S. Appl. No. 13/412,464 (US 2013/0230609), filed Mar. 5, 2012 (Sep. 5, 2013).

(Continued)

*Primary Examiner* — Terry A McKelvey
*Assistant Examiner* — Catheryne Chen
(74) *Attorney, Agent, or Firm* — Timothy H. Van Dyke; Judith A. Evans; Beusse Wolter Sanks & Maire

(57) ABSTRACT

Disclosed are compositions comprising antimicrobially effective low concentrations of benzyl alcohol, one or more essential oil and one or more botanical extract. The compositions of the application may be used in personal care products including wound care products or in veterinary use. In certain embodiments, compositions are provided having antimicrobial active agents that are substantially or essentially entirely derived from natural sources, thereby allowing the user to avoid harsh and/or toxic chemicals. This may be particularly advantageous in products for use by or on children or pets or for use in households or other environments occupied by children or animals.

2 Claims, No Drawings

Related U.S. Application Data a continuation-in-part of application No. 13/412,464, filed on Mar. 5, 2012.

(60) Provisional application No. 61/555,367, filed on Nov. 3, 2011, provisional application No. 61/567,372, filed on Dec. 6, 2011, provisional application No. 61/583,482, filed on Jan. 5, 2012, provisional application No. 61/583,505, filed on Jan. 5, 2012, provisional application No. 61/583,998, filed on Jan. 6, 2012.

(51) Int. Cl.
*A61K 36/28* (2006.01)
*A61Q 19/10* (2006.01)
*A61K 8/92* (2006.01)
*A01N 65/22* (2009.01)

(56) References Cited

U.S. PATENT DOCUMENTS

| | | |
|---|---|---|
| 4,330,531 A | 5/1982 | Alliger |
| 4,404,197 A | 9/1983 | Fox, Jr. et al. |
| 4,563,485 A | 1/1986 | Fox, Jr. et al. |
| 4,579,731 A | 4/1986 | Fox, Jr. et al. |
| 4,581,028 A | 4/1986 | Fox, Jr. et al. |
| 4,612,337 A | 9/1986 | Fox, Jr. et al. |
| 4,723,950 A | 2/1988 | Lee |
| 4,859,359 A | 8/1989 | DeMatteo et al. |
| 4,867,898 A | 9/1989 | Spaulding et al. |
| 4,956,354 A | 9/1990 | Gutierrez |
| 4,975,217 A | 12/1990 | Brown-Skrobot et al. |
| 5,019,096 A | 5/1991 | Fox, Jr. et al. |
| 5,033,488 A | 7/1991 | Curtis et al. |
| 5,073,366 A | 12/1991 | Beck |
| 5,091,442 A | 2/1992 | Milner |
| 5,100,652 A | 3/1992 | Kross |
| 5,135,747 A | 8/1992 | Faryniarz et al. |
| 5,180,605 A | 1/1993 | Milner |
| 5,200,194 A | 4/1993 | Edgren et al. |
| 5,209,251 A | 5/1993 | Curtis et al. |
| 5,261,421 A | 11/1993 | Milner |
| 5,310,546 A | 5/1994 | Douglas |
| 5,334,588 A | 8/1994 | Fox, Jr. et al. |
| 5,567,495 A | 10/1996 | Modak et al. |
| 5,614,538 A | 3/1997 | Nelson, Jr. |
| 5,616,338 A | 4/1997 | Fox, Jr. et al. |
| 5,772,640 A | 6/1998 | Modak et al. |
| 5,854,266 A | 12/1998 | Nelson, Jr. |
| 5,866,527 A | 2/1999 | Mertens |
| 5,891,422 A | 4/1999 | Pan et al. |
| 5,968,539 A | 10/1999 | Beerse et al. |
| 5,985,819 A | 11/1999 | Lu et al. |
| 5,985,918 A | 11/1999 | Modak et al. |
| 6,075,056 A | 6/2000 | Quigley, Jr. et al. |
| 6,083,208 A | 7/2000 | Modak et al. |
| 6,106,505 A | 8/2000 | Modak et al. |
| 6,120,758 A | 9/2000 | Siddiqui |
| 6,153,208 A * | 11/2000 | McAtee ............ A61K 8/0208 424/401 |
| 6,258,368 B1 | 7/2001 | Beerse et al. |
| 6,270,811 B1 | 8/2001 | Fregonese |
| 6,280,758 B1 | 8/2001 | Warren et al. |
| 6,287,583 B1 | 9/2001 | Warren et al. |
| 6,312,675 B1 | 11/2001 | Deane |
| 6,319,958 B1 | 11/2001 | Johnson et al. |
| 6,323,166 B1 | 11/2001 | Kamiya |
| 6,348,501 B1 | 2/2002 | Holt et al. |
| 6,397,224 B1 | 5/2002 | Zubeldia et al. |
| 6,420,326 B1 | 7/2002 | Maile et al. |
| 6,451,748 B1 | 9/2002 | Taylor et al. |
| 6,537,955 B1 * | 3/2003 | Raso ............ C11D 17/049 510/218 |
| 6,582,719 B2 | 6/2003 | Modak et al. |
| 6,616,922 B2 | 9/2003 | Taylor et al. |
| 6,630,163 B1 | 10/2003 | Murad |
| 6,632,784 B2 | 10/2003 | Massaux et al. |
| 6,635,676 B2 | 10/2003 | Baker, Jr. et al. |
| 6,696,399 B1 | 2/2004 | Chernin et al. |
| 6,699,825 B2 | 3/2004 | Rees et al. |
| 6,716,883 B1 | 4/2004 | Casper |
| 6,753,305 B2 | 6/2004 | Rasa et al. |
| 6,858,317 B2 | 2/2005 | Aamodt et al. |
| 6,921,745 B2 | 7/2005 | Yamada et al. |
| 6,951,833 B2 | 10/2005 | O'Neil |
| 6,969,522 B2 | 11/2005 | Bessette et al. |
| 6,974,584 B2 | 12/2005 | Bessette |
| 7,247,295 B2 | 7/2007 | Schmaus et al. |
| 7,435,429 B2 | 10/2008 | Modak et al. |
| 7,563,461 B2 | 7/2009 | Modak et al. |
| 7,563,462 B2 | 7/2009 | Modak et al. |
| 7,572,469 B2 * | 8/2009 | Santo ............ A61K 31/10 424/756 |
| 7,745,425 B2 | 6/2010 | Modak et al. |
| 7,871,649 B2 | 1/2011 | Modak et al. |
| 7,985,773 B2 | 7/2011 | Greten et al. |
| 2001/0010016 A1 | 7/2001 | Modak et al. |
| 2001/0024661 A1 | 9/2001 | Modak et al. |
| 2002/0122876 A1 | 9/2002 | Modak et al. |
| 2002/0165130 A1 | 11/2002 | Johnson et al. |
| 2002/0173775 A1 | 11/2002 | Modak et al. |
| 2002/0192256 A1 | 12/2002 | Wu et al. |
| 2003/0113388 A1 | 6/2003 | Phan |
| 2003/0168077 A1 | 9/2003 | Brown et al. |
| 2003/0180233 A1 | 9/2003 | Anderson et al. |
| 2003/0213168 A1 | 11/2003 | Hesse et al. |
| 2004/0092482 A1 | 5/2004 | Gupta |
| 2004/0102429 A1 | 5/2004 | Modak et al. |
| 2004/0132667 A1 | 7/2004 | Lintner |
| 2004/0192551 A1 | 9/2004 | Bessette et al. |
| 2004/0247685 A1 | 12/2004 | Modak et al. |
| 2004/0253275 A1 | 12/2004 | Eini et al. |
| 2005/0026802 A1 | 2/2005 | Kilkenny et al. |
| 2005/0048139 A1 | 3/2005 | Modak et al. |
| 2005/0063939 A1 | 3/2005 | Ameer et al. |
| 2005/0187124 A1 | 8/2005 | Li et al. |
| 2005/0222276 A1 | 10/2005 | Schmaus et al. |
| 2005/0238602 A1 | 10/2005 | Modak et al. |
| 2006/0018867 A1 | 1/2006 | Kawasaki et al. |
| 2006/0051384 A1 | 3/2006 | Scholz et al. |
| 2006/0099237 A1 | 5/2006 | Modak et al. |
| 2006/0198800 A1 | 9/2006 | Dilallo et al. |
| 2006/0216246 A1 | 9/2006 | Belanger et al. |
| 2006/0233901 A1 | 10/2006 | Jamieson et al. |
| 2006/0293201 A1 | 12/2006 | Simon et al. |
| 2006/0293214 A1 | 12/2006 | Cheng et al. |
| 2007/0003538 A1 | 1/2007 | Madhyastha |
| 2007/0014823 A1 | 1/2007 | Iwata et al. |
| 2007/0020342 A1 | 1/2007 | Modak et al. |
| 2007/0027119 A1 | 2/2007 | Ahmed et al. |
| 2007/0190094 A1 | 8/2007 | Bessette et al. |
| 2007/0275070 A1 | 11/2007 | Ahmed et al. |
| 2007/0286813 A1 | 12/2007 | Toutounghi |
| 2008/0008729 A1 | 1/2008 | Swaine et al. |
| 2008/0038219 A1 | 2/2008 | Mosbaugh et al. |
| 2008/0063607 A1 | 3/2008 | Tamarkin et al. |
| 2008/0166314 A1 | 7/2008 | Jochim et al. |
| 2008/0226568 A1 | 9/2008 | Rozsa et al. |
| 2008/0234173 A1 | 9/2008 | Warr et al. |
| 2008/0253976 A1 | 10/2008 | Scott et al. |
| 2008/0260708 A1 | 10/2008 | Hall |
| 2008/0299220 A1 | 12/2008 | Tamarkin et al. |
| 2008/0311231 A1 | 12/2008 | Modak et al. |
| 2008/0317737 A1 | 12/2008 | Patel et al. |
| 2008/0318784 A1 | 12/2008 | Koo et al. |
| 2009/0004122 A1 | 1/2009 | Modak et al. |
| 2009/0028751 A1 | 1/2009 | Robbins |
| 2009/0029961 A1 | 1/2009 | Modak et al. |
| 2009/0035228 A1 | 2/2009 | Modak et al. |
| 2009/0068255 A1 | 3/2009 | Yu et al. |
| 2009/0088358 A1 | 4/2009 | Roso et al. |
| 2009/0165812 A1 | 7/2009 | Resnick et al. |
| 2009/0175806 A1 | 7/2009 | Modak et al. |

(56) References Cited

U.S. PATENT DOCUMENTS

| | | |
|---|---|---|
| 2009/0191288 A1 | 7/2009 | Squires et al. |
| 2009/0300864 A1 | 12/2009 | Adkins, Jr. et al. |
| 2010/0034871 A1 | 2/2010 | Mikkelsen et al. |
| 2010/0093595 A1 | 4/2010 | Holzhauer et al. |
| 2010/0140368 A1 | 6/2010 | De Lame et al. |
| 2010/0172847 A1 | 7/2010 | Modak et al. |
| 2010/0172848 A1 | 7/2010 | Modak et al. |
| 2010/0183524 A1 | 7/2010 | Zielinski et al. |
| 2010/0196494 A1 | 8/2010 | Van Beek |
| 2010/0216889 A1 | 8/2010 | Modak et al. |
| 2010/0234460 A1 | 9/2010 | Foret et al. |
| 2010/0248962 A1 | 9/2010 | Wilczynski et al. |
| 2010/0317743 A1 | 12/2010 | Macinga et al. |
| 2010/0323043 A1 | 12/2010 | Perla et al. |
| 2011/0028563 A1 | 2/2011 | Found |
| 2011/0070376 A1 | 3/2011 | Wales et al. |
| 2011/0142899 A1 | 6/2011 | Lagaron Abello et al. |
| 2012/0100231 A1 | 4/2012 | Marc et al. |
| 2012/0129950 A1 | 5/2012 | Macinga et al. |
| 2012/0171156 A1 | 7/2012 | Basketter et al. |
| 2012/0201902 A1 | 8/2012 | Modak et al. |
| 2012/0207862 A1 | 8/2012 | Morre et al. |
| 2013/0230609 A1 | 9/2013 | Modak et al. |
| 2014/0079819 A1 | 3/2014 | Debaun et al. |
| 2014/0178447 A1 | 6/2014 | Modak et al. |
| 2014/0242198 A1 | 8/2014 | Modak et al. |
| 2014/0243417 A1 | 8/2014 | Modak et al. |
| 2014/0287072 A1 | 9/2014 | Modak et al. |
| 2014/0322147 A1 | 10/2014 | Modak et al. |

FOREIGN PATENT DOCUMENTS

| | | |
|---|---|---|
| DE | 202008002718 U1 | 7/2009 |
| EP | 0 054 205 | 6/1982 |
| EP | 0 106 266 | 4/1984 |
| EP | 0231080 A1 | 8/1987 |
| EP | 1108419 | 6/2001 |
| EP | 1 146 112 | 10/2001 |
| EP | 1206933 | 5/2002 |
| EP | 1 288 285 | 3/2003 |
| FR | 2771632 | 6/1999 |
| FR | 2874928 | 3/2010 |
| GB | 1 060 447 | 3/1967 |
| JP | 1997-323910 | 12/1997 |
| JP | 2002-193717 | 7/2002 |
| JP | 2002-370958 | 12/2002 |
| JP | 2004-217615 | 8/2004 |
| JP | 04250331 | 9/2004 |
| JP | 2004277554 | 10/2004 |
| JP | 2004-322078 | 11/2004 |
| JP | 2006-225289 | 8/2006 |
| JP | 2007-291049 | 11/2007 |
| JP | 2010-083806 | 4/2010 |
| JP | 2010-184987 | 8/2010 |
| KR | 10-2004-077206 | 9/2004 |
| SU | 513676 | 5/1976 |
| WO | WO 1984/004556 | 11/1984 |
| WO | WO 1985/0001208 | 3/1985 |
| WO | WO 1989/0006962 | 8/1989 |
| WO | WO 1992/0004029 | 3/1992 |
| WO | 93/02717 A1 | 2/1993 |
| WO | WO 1993/002717 | 2/1993 |
| WO | WO 1998/051273 | 11/1998 |
| WO | WO 1999/022718 | 5/1999 |
| WO | WO 2000/065011 | 11/2000 |
| WO | WO 2001/072262 | 10/2001 |
| WO | WO 01/91555 | 12/2001 |
| WO | WO 2002/022060 | 3/2002 |
| WO | WO 2003/000303 | 1/2003 |
| WO | WO 2003/018498 | 3/2003 |
| WO | WO 2003/018743 | 3/2003 |
| WO | WO 2003/077856 | 9/2003 |
| WO | WO 2003/078367 | 9/2003 |
| WO | WO 2004/004631 | 1/2004 |
| WO | WO 2004/014416 | 2/2004 |
| WO | WO 2006/010269 | 2/2006 |
| WO | WO 2006/023349 | 3/2006 |
| WO | WO 2006/099359 | 9/2006 |
| WO | WO 2007/069214 | 6/2007 |
| WO | WO 2007/071089 | 6/2007 |
| WO | WO 2007/077573 | 7/2007 |
| WO | WO 2007/095041 | 8/2007 |
| WO | WO 2007/0101848 | 9/2007 |
| WO | WO 2007/123790 | 11/2007 |
| WO | WO 2007/0126651 | 11/2007 |
| WO | WO 2008/031087 | 3/2008 |
| WO | WO 2008/0042197 | 4/2008 |
| WO | WO 2008/061187 | 5/2008 |
| WO | WO 2008/0119841 | 10/2008 |
| WO | WO 2008/0154395 | 12/2008 |
| WO | WO 2008/0157847 | 12/2008 |
| WO | WO 2009/062746 | 3/2009 |
| WO | WO 2009/049208 | 4/2009 |
| WO | WO 2010/091415 | 8/2010 |
| WO | WO 2010/0119369 | 10/2010 |
| WO | WO 2011/002929 | 1/2011 |
| WO | 2011/151835 A1 | 12/2011 |
| WO | WO 2011/151835 | 12/2011 |
| WO | WO 2012/017349 | 2/2012 |
| WO | WO 2012/051204 | 4/2012 |
| WO | 2013/066403 A1 | 5/2013 |
| WO | 2013/103556 A1 | 7/2013 |
| WO | WO 2014/092999 | 6/2014 |

OTHER PUBLICATIONS

U.S. Appl. No. 14/267,403, filed May 1, 2014.
U.S. Appl. No. 14/294,933, filed Jun. 3, 2014.
U.S. Appl. No. 12/694,119, filed Dec. 21, 2012 Amendment and Request for Continued Examination (RCE).
U.S. Appl. No. 12/694,119, filed Jun. 22, 2012 Final Office Action.
U.S. Appl. No. 12/694,119, filed Jan. 12, 2012 Response to Non-Final Office Action.
U.S. Appl. No. 12/694,119, filed Oct. 12, 2012 Non-Final Office Action.
U.S. Appl. No. 12/016,788, filed Aug. 24, 2012 Final Office Action.
U.S. Appl. No. 12/016,788, filed Apr. 24, 2012 Response to Non-Final Office Action.
U.S. Appl. No. 12/016,788, filed Oct. 24, 2012 Non-Final Office Action.
U.S. Appl. No. 12/134,918, filed Jan. 31, 2013 Amendment and Request for Continued Examination (RCE).
U.S. Appl. No. 12/134,918, filed Jul. 31, 2012 Final Office Action.
U.S. Appl. No. 12/134,918, filed Mar. 28, 20102 Response to Non-Final Office Action.
U.S. Appl. No. 12/134,918, filed Nov. 15, 2011 Non-Final Office Action.
U.S. Appl. No. 12/694, 141, filed Jul. 24, 2012 Final Office Action.
U.S. Appl. No. 12/694,141, filed Mar. 28, 2012 Response to Non-Final Office Action.
U.S. Appl. No. 12/694,141, filed Nov. 28, 2011 Non-Final Office Action.
U.S. Appl. No. 12/134,911, filed May 2, 2012 Amendment and Request for Continued Examination (RCE).
U.S. Appl. No. 12/134,911, filed Dec. 2, 2011 Final Office Action.
U.S. Appl. No. 12/134,911, filed Aug. 18, 2011 Response to Non-Final Office Action.
U.S. Appl. No. 12/134,911, filed Feb. 18, 2011 Non-Final Office Action.
U.S. Appl. No. 12/136,530, filed Feb. 1, 2012 Notice of Abandonment.
U.S. Appl. No. 12/136,530, filed Jun. 29, 2011 Non-Final Office Action.
U.S. Appl. No. 13/335,363, filed Feb. 19, 2013 Non-Final Office Action.
U.S. Appl. No. 12/016,788, filed Feb. 22, 2013 Amendment and Request for Continued Examination (RCE).
U.S. Appl. No. 12/016,788, filed Aug. 1, 2013 Non-Final Office Action.

(56) References Cited

OTHER PUBLICATIONS

U.S. Appl. No. 13/335,363, filed Nov. 1, 2013 Final Office Action.
U.S. Appl. No. 13/335,363, filed Aug. 15, 2013 Response to Non-Final Office Action.
U.S. Appl. No. 12/134,918, filed Nov. 7, 2013 Non-Final Office Action.
U.S. Appl. No. 12/694,119, filed Jun. 26, 2014 Non-Final Office Action.
U.S. Appl. No. 12/016,788, filed Jun. 19, 2014 Final Office Action.
U.S. Appl. No. 13/335,363, filed Apr. 1, 2014 Amendment and Request for Continued Examination (RCE).
U.S. Appl. No. 13/412,464, filed Jul. 7, 2014 Response to Non-Final Office Action.
U.S. Appl. No. 12/134,918, filed May 7, 2014 Response to Non-Final Office Action.
Entry for "citral" in Merck Index, 14th Edition.
Entry for Lemongrass oil, downloaded Jul. 15, 2012 from internet site: https://www.essentialoils.co.za/essential-oils/lemongrass.htm.
Entry for Orange Oil, downloaded Jul. 15, 2012 from internet site: https://www.essentialoils.co.za/essential-oils/orange.htm.
Judžentiené, et al., "Characterisitcs of essential oil composition in the needles of young Scots pine (*Pinus sylvestris* L.) stands growing along an aerial ammonia gradient", *Chemija*, 17(4):67-73, 2006.
Kurita, et al., "Synergistic Antimicrobial Effect of Ethanol, Sodium Chloride, Acetic Acid and Essential Oil Components", *Agricultural Biology Chemistry*, 47(1):67-75, 1983.
Mohammad Najmul Ghani Khan; Khazaain-al-Advia, vol. II (20th century AD), Nadeem Yunus Printer/Sheikh Mohd Basheer & Sons, Lahore, 1911 AD p. 656.
Mohammad Najmul Ghani Khan; Qaraabaadeen Najm-al-Ghani (20th century AD), Munshi Nawal Kishore, Lucknow, (Second Edition) 1928 AD p. 566.
Mohammad Azam Khan; Muheet Azam vol. II (Part II) (19th century AD), Matba Nizami, Kanpur, 1898 AD p. 3.
Susruta; Susruta Samhita—Edited & translated by P.V. Sharma, vol. III: Chaukhamba Visvabharati, Varanasi, Edn. 1st, 2001. [Time of origin 1000 BC—5th century] p. 10.
Mohammad Azam Khan; Muheet-e-Azam vol. III (19th century AD), Matba Nizami, Kanpur, 1887 AD p. 261.
Mohammad Shareef Khan; Ilaaj-al-Amraaz (18th centruy AD), Afzal-al-Matabe, Barqi Press, Delhi, 1921 AD p. 357.
Siddhayogasamgrahah—Compiled by Yadavji Trikamji Acharya, Sri Baidyanath Ayurved Bhawan, Allahabad, Edn. 1st 1978 pp. 131-132.
Mohammad Najmul Ghani Khan; Khazaain-al-Advia, vol. III (20th century AD), Nadeem Yunus Printer/Sheikh Mohd Basheer & Sons, Lahore, 1926 AD p. 568.
Sarngadharacarya; Saringadhara Samhita—Translated by Smt. Shailaja Srivastava: Chaukhamba Orientalia, Varansai, Edn. 2nd, 1998. [Time of origin 13th century] pp. 431-432.
Ziya Al-Din Abdullah Ibn Al-Baitar; Al-Jaam'e-li-Mufradaat-al-Advia-wal-Aghzia, vol. IV (13th century AD), Matba Amra, Cario, Egypt, 1874 AD p. 57.
Abu Bakr Mohammad, Bin Zakariyya Al-Razi; Kitaab-al-Haawi-fil-Tibb, vol. ii (9th century AD), Dayerah-Al-Ma'aarof Is,amoa. Juderabad. 1976 AD p. 434.
Mohammad Shareef Khan; Ilaaj-al-Amraaz (18th centruy AD), Afzal-al-Matabe, Barqi Press, Delhi, 1921 AD p. 335.
Mohammad Azam Khan; Muheet-e-Azam vol. III (19th century AD), Matba Nizami, Kanpur, 1887 AD p. 69.
Mohammad Najmul Ghani Khan; Khazaain-al-Advia, vol. II (20th century AD), Nadeem Yunus Printer/Sheikh Mohd Basheer & Sons, Lahore, 1911 AD p. 657.
Mohammad Azam Khan; Muheet-e-Azam vol. 1 (19th century AD), Matba Nizami, Kanpur, 1896 AD p. 257.
Cakrapanidattah; Cakradattah—Translated by Indradeva Tripathi; Chaukhamba Sanskrit Samsthan (Varanasi), Ed. 4th 2002, p. 260.
Baiju, et al., "Development of a Novel Surface Disinfectant Composition Containing Essential Oils and Fruit Acid Against Nosocomial Pathogens Commonly Associated with Environmental Surfaces", *International Journal of Essential Oil Therapeutics*, vol. 2:9-14 (2008).
Bezic, et al., "Composition and antimicrobial activity of *Achillea clavennae* L. essential oil." *Phytother. Res.* 17(9):1037-1040 (2003).
Bion, 2008, "Acne Treatment Products" http://www.bion-research.com/acne_treatment_products.htm.
Bion, 2008, "Moderate to Severe Acne" http://www.bion-research.com/moderate_to_severe_acne.htm.
Brehm-Stecher et al., "Sensitization of *Staphylococcus aureus* and *Escherichia coli* to antibiotics by the sesquiterpenoids nerolidol, farnesol, bisabolol, and apritone", *Antimicrobial Agents and Chemotherapy*; 47(10):3357-3360 (2003).
de Abreu Gonzaga et al., "Composition and antibacterial activity of the essential oils from Zanthoxylum rhoifolium", *Planta Med.* 69(8):773-775 (2003).
Garcia, et al.; "Virucidal activity of essential oils from aromatic plants of San Luis, Argentina", *Phytother. Res.*, 17(9):1073-1075 (2003).
Gershon, et al., "Antifungal Properties of n-Alkanols, α, w-n-Alkanedoils, and w-Chloro-α-alkanols", *J. Pharm. Sci.*, 64(4):381-384 (2006).
Goren, et al., "Analysis of essential oil of *Coridothymus capitates* (L.) and its antibacterial and antifungal activity", *Z. Naturforsch.*, 58(9-10):687-690 (2003).
Hajhashemi, et al., "Anti-inflammatory and analgesic properties of the leaf extracts and essential oil of Lavandula angustifolia Mill", *J. Ethnopharmacol.* 89(1):67-71 (2003).
Kupferwasser, et al., "Acetylsalicylic Acid Reduces Vegetation Bacterial Density, Hematogenous Bacterial Dissemination, and Frequency of Embolic Events in Experimental *Staphylococcus aureus* Endocarditis Through Antiplatelet and Antibacterial Effects", *Circulation*, vol. 99:2791-2797 (1999).
Kupferwasser, et al., "Salicylic Acid Attenuates Virulence in Endovascular Infections by Targeting Global Regulatory Pathways in *Staphylococcus aureus,*" *Clin. Invest.*, 112(2):222-233 (2003).
Minami et al., "The inhibitory effect of essential oils on herpes simplex virus type-1 replication in vitro", *Microbial Immunol.* 47(a):681-684 (2003).
Paranagama et al., "Fungicidal and anti-aflatoxigenic effects of the essential oil of Cymbopogon citratus (DC.) Stapf. (lemongrass) against Aspergillus flavus Link. isolated from stored rice", *Lett. Appl. Microbiol.*; 37(1):86-90 (2003).
Schuhmacher, et al., "Virucidal effect of peppermint oil on the enveloped viruses herpes simplex virus type 1 and type 2 in vitro", *Phytomedicine.*, 10:504-510 (2003).
Shin, "Anti-Aspergillus activities of plant essential oils and their combination effects with ketoconazole or amphotericin B", *Arch. Pharm. Res.*, 26(5):389-393 (2003).
Silva et al.,"Analgesic and anti-inflammatory effects of essential oils of Eucalyptus", *J. Ethnopharmacol.*, 89(2-3);277-283 (2003).
Valero, et al.,, "Antibacterial activity of 11 essential oils against Bacillus cereus in tyndallized carrot broth", *Int. J. Food Microbiol.*, 85(1-2):73-81 (2003).
Velluti, et al., "Inhibitory effect of cinnamon, clove, lemongrass, oregano and palmarose essential oils on growth and fumonisin B1 production by Fusarium proliferatum in maize grain." *Int. J. Food Microbiol.*, 89:145-154 (2003).
Ayliffe, et al., "Hand disinfection: A comparison of various agents in laboratory and ward studies", *Journal of Hospital Infection*, 11(3):226-243 (1988).
Bettini Mercia de Fatima M., "Purification of Orange Peel Oil and Oil Phase by Vacuum Distillation", *Functional Food Ingredients and Nutraceuticals, Processing Technologies, Edited by john Shi, CRC Press* 2006, pp. 157-172.
Cancio, et al., "Burn wound infections" In: *Surgical Treatment: Evidence-Based and Problem-Oriented*, 2001.
Fang, et al., "Prospective clinical study of Hydron, a synthetic dressing, in delivery of an antimicrobial drug to second-degree burns", *J Burn Care Rehabil.*, 8(3):206-209 (1987).
Fox, et al., "Comparative evaluation of zinc sulfadiazine and silver sulfadiazine in burn wound infection", *J. Burn Care Rehabil.*, 11(2):112-117 (1990).

(56) References Cited

OTHER PUBLICATIONS

Gaonkar, et al., "In vivo efficacy of an alcohol-based surgical hand disinfectant containing a synergistic combination of ethylhexylglycerin and preservatives", *Journal of Hospital Infection*, 63(4):412-417 (2006).
Gaonkar, et al., "An alcohol hand rub containing a synergistic combination of an emollient and preservatives: prolonged activity against transient pathogens", *Journal of Hospital Infection*, 59(1):12-18 (2005).
European Supplementary Search Report for EP 08780771.5, dated Dec. 17, 2012.
International Search Report and Written Opinion for PCT/US2012/052793, dated Nov. 19, 2012.
International Search Report and Written Opinion for PCT/US2012/063013, dated Jan. 4, 2013.
International Search Report and Written Opinion for PCT/US2012/037135, dated Oct. 16, 2012.
Choudhary, et al., "Solvent-free selective oxidation of benzyl alcohol and benzaldehyde by tert-butyl hydroperoxide using $MnO_4$-exchanged Mg-Al-hydrotalcite catalsysts", *Catalysis Letters*, 86(4):229-233 (2003).
Zhang, et al., "Antifungal Activities of Major Tea Leaf Volatile Constituents toward Colletorichum Camelliae Massea", *Journal of Agricultural and Food Chemistry*, 54(11):3936-3940 (2006).
Nazer, et al., "Combinations of food antimicrobials at low levels to inhibit the growth of *Salmonella* sv. Typhimurium: a synergistic effect?", *Food Microbiology*, 22:391-398 (2005).
"Sheer Moisturizer Hand Sanitizer", *Mintel Global New Products Database*, pp. 1-4 (2010) Retrieved from the Internet: URL:www.gnpd.com [Retrieved on Aug. 34, 2013].
"Antibacterial Wet Wipes", *Mintel Global New Products Database*, pp. 1-2 (2008) Retrieved from the Internet: URL:www.gnpd.com [Retrieved on Sep. 24, 2013].
Cowan, "Plant product as antimicrobial agents", *Clinical Microbiology Reviews*, 12(4):564-582 (1999).
Nannapaneni et al., "Antimicrobial activity of commercial citrus-based natural extracts against *Escherichia coli* O157:H7 isolates and mutant strains", *Foodborne Pathog Dis.*, 5(5):695-699 (2008).
International Search Report and Written Opinion for PCT/US2013/071731, dated Feb. 12, 2014.
Keeven et al., "Evaluating the preservative effectiveness of RGP lens care solutions", *The Contact Lens Association of Ophthalmologists Journal*, 21(4):238-241 (1995).
El-Zemity et al., "Antifungal activity of some essential oils and their major chemical constituents against some phytopathogenic fungi", *Journal of Pest Control and Enviromental Science*, 13(1):87-99 (2005).
U.S. Appl. No. 14/323,843 (US 2014/0322147), filed Jul. 3, 2014 (Oct. 30, 2014).
U.S. Appl. No. 12/134,918, filed Aug. 28, 2014 Final Office Action.
U.S. Appl. No. 13/335,363, filed Sep. 2, 2014 Non-Final Office Action.
U.S. Appl. No. 13/412,464, filed Oct. 17, 2014 Final Office Action.
Khazaain-al-Advia vol. III (20th century AD), Mohammad Najmul Ghani Khan, Nadeem Yunus Printer/Sheikh Mohd Basheer & Sons, Lahore, 1926 AD p. 1050.
Qaraabaadeen Najm-al-Ghani (20th century AD), Mohammad Najmul Ghani Khan, Munshi Nawal Kishore, Lucknow, (Second Edition) 1928 AD p. 492.
Khazaain-al-Advia vol. II (20th century AD), Mohammad Najmul Ghani Khan, Nadeem Yunus Printer/Sheikh Mohd Basheer & Sons, Lahore, 1911 AD p. 657.
Kitaab-al-Umdah-fil-Jeraahat, Part I (13th century AD), Aminuddaulah Abul Farj Ibn Al-Quff Maseehi; Dayerah-al-Ma'aarif Usmania, Hyberabad, 1937 AD p. 234-235.
Ziya Al-Din Abdullah Ibn Al-Baitar; al-Jaam'e-li-Mufradaat-al-Advia-wal-Aghzia, vol. II (13th century AD), Matba Amra, Cairo, Egypt, 1874 AD p. 84.
Sodhalanighantauh—(Namasamgraha Va Gunasamgraha) Sodhala; Edited by P.V. Sharma, Oriental Institute, Broda, Edn $1^{st}$ 1978 p. 116.
Khazaain-al-Advia vol. II (20th century AD), Mohammad Najmul Ghani Khan, Nadeem Yunus Printer/Sheikh Mohd Basheer & Sons, Lahore, 1911 AD p. 342-343.
Kitaab-al-Haawi-fil-Tibb, vol. IX (9th century AD), Abu Bakr Mohammad Bin Zakariyya Al-Razi; Dayerah-al-Ma'aarif Usmania, Hyberabad, (First Edition) 1960 AD p. 194.
Khazaain-al-Advia, vol. I ($20^{th}$ century AD) Mohammad Najmul Ghani Khan; Nadeem Yunus Printer/Sheikh Mohd Basheer & Sons, Lahore, 1911 AD p. 669.
Vagabhata; Astanga Hrdaya—(commentary by Arunadutta) edited by Bhisagacarya Harisastri Paradakara Vaidya; Chaukhamba Orientalia, Varanasi, edn. $8^{th}$, 1998 [Time of origin $5^{th}$ century] p. 890.
Mohammad Azam Khan; Muheet-e-Azam, vol. I ($19^{th}$ century AD), Matba Nizami, Kanpur, 1896 AD p. 197.
International Search Report and Written Opinion for PCT/US14/29486, dated Oct. 10, 2014.
Biosecur Lad Inc., "Biosecur™ Product Line Receives Self-Affirmed Gras Status for Use as an antioxidant and Nutrient Supplement", Biosecur News Release 030811, Mar. 10, 2011, (2 pages).
Hazan et al., "Benzoic Acis, a Weak Organic Acid Food Preservative, Exerts specific Effects on Intracellular Membrane Trafficking Pathways in *Saccharomyces cerevisiae* ", Appl. Environ. Microbiol., 70(8):4449 (2004).
Song, et al., "Volatiles from Ficus hispida and their attractiveness to fig wasps", Journal of Chemical Ecology, 27:1929-1942 (2001).
Komthong et al., "Ascending bubble extraction of terpenes from freshly squeezed orange juice", Food Research International, 39:53-58 (2006).
Kumar et al., "Assessment of *Thymus vulgaris* L. essential oil as a safe botanical preservative against post harvest fungal infestation of food commodities", Innovative Food Science & Emerging Technologies, 9(4):575-580 (Oct. 2008).
Gemeda et al., "Effect of essential oils on aspergillus spore germination, growth and mycotoxin production: a potential source of botanical food preservative", APJTB, 4(Suppl. 1):5373-381 (May 2014).
U.S. Appl. No. 12/134,918 dated Apr. 22, 2015 Non-Final Office Action.
U.S. Appl. No. 12/694,119 dated May 8, 2015 Final Office Action.
U.S. Appl. No. 12/016,788 dated Mar. 6, 2015 Non-Final Office Action.
U.S. Appl. No. 12/016,788 dated Jun. 2, 2015 Response to Non-Final Office Action.
Baratta, et al., "Antimicrobial and antioxidant properties of some commercial essential oils", Flavour Fragr. J., 13, 235±244 (1998).
Biosource Naturals, product sheet for Lemongrass oil. Downloaded Apr. 5, 2015, from http://www.biosourcenaturals.com/lemongrass-essential-oil.htm.
Fact Sheet on Basil oil from Chemical Book, Downloaded Apr. 5, 2015, from http://www.chemicalbook.com/ChemicalProductProperty_US_CB3405198.aspx.
Prabuseenivasan, et al., "In vitro antibacterial activity of some plant essential oils", BMC Complementary and Alternative Medicine 2006, 6:39, pp. 1-8.
Skin Care, retrieved from URL:<https://web.archive.org/web/20050119140921/http://www.morganics.com/store/page8.html>, Jan 19, 2005.
Subba, et al., "Antimicrobial Action of Citrus Oils" J. Food Sci. 1967, vol. 32, pp. 225-227.
Wilson, et al., "The quantification of citral in lemongrass and lemon oils by near-infrared spectroscopy", Journal of Pharmacy and Pharmacology 2002, 54: 1257-1263.
U.S. Appl. No. 12/016,788 dated Oct. 22, 2015 Final Office Action.
U.S. Appl. No. 12/134,918 dated Jul. 31, 2015 Response to Non-Final Office Action.
U.S. Appl. No. 12/134,918 dated Nov. 4, 2015 Final Office Action.
U.S. Appl. No. 13/335,363 dated Jul. 8, 2015 Non-Final Office Action.

(56) References Cited

OTHER PUBLICATIONS

U.S. Appl. No. 13/412,464 dated Jun. 22, 2015 Final Office Action.
U.S. Appl. No. 12/134,911 dated Sep. 8, 2014 Notice of Allowance.
U.S. Appl. No. 12/134,911 dated Dec. 8, 2014 Issue Fee Payment.
"Lemongrass Oil: Lighten Up Your Mood with This All-Around Oil", Herbal Oil: Lemongrass Oil Benefits and Uses, 4 pages, 2015. http://articles.mercola.com/herbal-oils/lemongrass-oil.aspx.
Anand, et al., "Biological activities of curcumin and its analogues (Congeners) made by man and Mother Nature" Biochemical Pharmacology, 2008, vol. 76, pp. 1590-1611.
Bagamboula, et al., "Inhibitory effect of thyme and basil essential oils, carvacrol, thymol, estragol, linalool and p-cymene towards Shigella sonnei and S. flexneri" Food Microbiology 21 (2004) 33-42.
Chalchat, et al., Chemical Composition of Essential Oil of *Calendula oficinalis* L. (Pot Marigold). Flavour and Fragrance Journal, vol. 6, 189-192 (1991).
Chang, et al., Resources and bioactive substances from Taiwania (Taiwania cryptomerioides). J. Wood Sci (2003) 49:1-4.
Collins, et al., "A review of alternatives to organophosphorus compounds for the control of storage mites", Journal of Stored Products Research, vol. 42, No. 4, Jan. 1, 2006, pp. 395-426, XP028024314.
DailyMed Antiseptic skin cleanser—Chlorhexidine gluconate, Drug Label Information, updated Sep. 2012.
Nerio, et al., "Repellant activity of essential oils: A review", Biosource Technology, vol. 101, No. 1, Jan. 1, 2010, pp. 372-378, XP026624017.
Panchatcharam, et al., "Curcumin improves wound healing by modulating collagen and decreasing reactive oxygen species", Molecular and Cellular Biochemistry, vol. 290, No. 1-2, Jun. 13, 2006, pp. 87-96, XP019436632.
Reagor, et al., "The Effectiveness of Processed Grapefruit-Seed Extract as an Antibacterial Agent: I. An In Vitro Agar Assay" The Journal of Alternative and Complementary Medicine, 2002, vol. 8, pp. 325-332.
Supplementary Partial European Search Report dated Aug. 12, 2015 in Application No. 12846062.3.
Table of Acids with Ka and pKa, Downloaded Sep. 28 from the site: Downloaded Sep. 28, 2015, from http://cla.sa.ucsb.edu/staff/Resource%20folder/Chem109ABC/Acid,%20Base%20Strength/Table%20of%20Acids%20w%20Kas%20and%20pKas.pdf.
Zeus Quimica, "Zemea Propanediol", Information sheet, downloaded Jun. 24, 2015.
U.S. Appl. No. 14/564,920, filed Dec. 9, 2014.
U.S. Appl. No. 12/016,788, Dec. 18, 2014 Amendment and Request for Continued Examination.
U.S. Appl. No. 12/016,788, Mar. 6, 2015 Non-Final Office Action.
U.S. Appl. No. 12/016,788, Jun. 2, 2015 Response to Non-Final Office Action.
U.S. Appl. No. 12/134,918, Jan. 26, 2015 Amendment and Request for Continued Examination.
U.S. Appl. No. 12/134,918, Apr. 22, 2015 Non-Final Office Action.
U.S. Appl. No. 12/694,119, Dec. 18, 2014 Response to Non-Final Office Action.
U.S. Appl. No. 12/694,119, May 8, 2015 Final Office Action.
U.S. Appl. No. 13/412,464, Feb. 17, 2015 Amendment and Request for Continued.
U.S. Appl. No. 13/412,464, Apr. 20, 2015 Non-Final Office Action.
U.S. Appl. No. 13/412,464, Jun. 8, 2015 Response to Non-Final Office Action.
U.S. Appl. No. 13/335,363, Dec. 18, 2014 Response to Non-Final Office Action.
U.S. Appl. No. 13/335,363, Mar. 4, 2015 Final Office Action.
U.S. Appl. No. 13/335,363, Apr. 28, 2015 Amendment and Request for Continued Examination.
EP Office Action dated Dec. 2, 2014 in EP Application No. 10 794 733.5.
U.S. Appl. No. 12/694,119, Feb. 2, 2016 Applicant Initiated Interview Summary.
U.S. Appl. No. 12/694,119, Jan. 20, 2016 Non-Final Office Action.
Tecophilic TPU—LifeScience Polymers—The Lubrizol Corporation; "Tecophilic TPU"; https://web.archive.org/web/20140923074123/http://www.lubrizol.com/LifeScience/Products/Tecophilic.html; Sep. 23, 2014 [downloaded from internet Jan. 12, 2016]: entire document.
Baratta, M.T., et al., "Antimicrobial and antioxidant properties of some commercial essential oils," Flavour and Fragrance Journal 1998, pp. 235-244, vol. 13.
Block, S.S., "Disinfection, Sterilization, and Preservation; Fourth Edition," 1991, Pages Cover, 280-281 and 892, Publisher: Lea & Febiger.
EPO: Extended Search Report, European Patent Application No. 12845196.0, dated Sep. 5, 2016, pp. 1-8.
EPO: Supplementary Partial Search Report, European Patent Application No. 12845196.0, dated May 17, 2016, pp. 1-6.
EPO: Supplementary Search Report, European Patent Application No. 128460623, dated Jan. 8, 2016, pp. 1-14.
EPO: Supplementary Search Report, European Patent Application No. 147631923, dated Jan. 5, 2017, pp. 1-7.
ISA/US: International Search Report and Written Opinion, International Patent Application No. PCT/US15/62454, dated Feb. 9, 2016, pp. 1-12.
IP Australia: Patent Examination Report No. 1, Australian Patent Application No. 2012332495, dated Jun. 10, 2016, pp. 1-3.
Jabra-Rizk, M.A., et al., "Effects of Farnesol on *Staphlyococcus aureus* Biofilm Formation and Antimicrobial Suspectibility," Antimicrobial Agents and Chemotherapy 2006, pp. 1463-1469, Publisher: American Society for Microbiology.
JPO: Rejection, Japanese Patent Application No. 2014-539926, dated Jan. 19, 2016, 17 pages.
Pommier, P., et al., "Phase III Randomized Trial of Calendula Officinalis Compared With Trolamine for the Prevention of Acute Dermatitis During Irradiation for Breast Cancer," J Clin Oncol 2004, pp. 1447-1453, vol. 22, No. 8.
Watts, J. L, et al., "Evaluation of Test Dips with Excised Teats," Journal of Dairy Science 1984, pp. 2062-2065, vol. 67, Issue 9.
U.S. Appl. No. 12/955,432 (US 2011/0070316), filed Nov. 29, 2010 (Mar. 24, 2011).
U.S. Appl. No. 14/735,051 (US 2015/0265666), filed Jun. 9, 2015 (Sep. 24, 2015).
U.S. Appl. No. 14/194,381 (US 2014/0178447), filed Feb. 28, 2014 (Jun. 26, 2014).
U.S. Appl. No. 12/694,119, Nov. 5, 2015 Amendment and Request for Continued Examination (RCE).
U.S. Appl. No. 13/412,464, Sep. 11, 2015 Notice of Appeal Filed.
U.S. Appl. No. 14/194,381, Jan. 4, 2016 Non-Final Office Action.
U.S. Appl. No. 14/267,403, Nov. 17, 2015 Non-Final Office Action.
U.S. Appl. No. 14/294,933, Dec. 17, 2015 Non-Final Office Action.
Klaric et al., "Antifungal activity of thyme (*Thymus vulgaris* L.) essential oil and thymol against moulds from damp dwellings", 2006, The Society for Applied Microbiology, Letters in Applied Microbiology 44 (2007) 36-42.
Tayyem et al., "Curcumin Content of Turmeric and Curry Powders", Nutrition and Cancer, 55(2), 126-131, 2006.

\* cited by examiner

BOTANICAL ANTIMICROBIAL COMPOSITIONS

PRIORITY CLAIM

The present application is a continuation of International Application No. PCT/US12/037,135, filed May 9, 2012, which is a continuation-in-part of U.S. patent application Ser. No. 13/412,464, filed Mar. 5, 2012; and also claims priority to U.S. Provisional Patent Application Ser. No. 61/555,367, filed Nov. 3, 2011, U.S. Provisional Patent Application Ser. No. 61/567,372, filed Dec. 6, 2011, U.S. Provisional Patent Application Ser. No. 61/583,482, filed Jan. 5, 2012, U.S. Provisional Patent Application Ser. No. 61/583,505, filed Jan. 5, 2012, and U.S. Provisional Patent Application Ser. No. 61/583,998, filed Jan. 6, 2012; to each of which priority is claimed and all of which are incorporated herein by reference in their entireties.

1. INTRODUCTION

Disclosed are compositions comprising antimicrobially effective combinations of benzyl alcohol, essential oils and botanical extracts (including plant extracts and fruit extracts).

2. BACKGROUND

Essential oils are volatile oils obtained from plant or animal sources and are composed of complex mixtures of several constituents, such as monoterpenes and sesquiterpene hydrocarbons, monoterpene and sesquiterpene alcohols, esters, ethers, aldehydes, ketones, oxides and the like. These essential oils and their isolated constituents are frequently utilized as fragrance and flavor agents, and have been widely used in folk medicine for wound healing properties.

Scientific research has corroborated the beneficial effects of essential oils. Essential oils of eucalyptus have been found to "possess central and peripheral analgesic effects as well as neutrophil-dependent and independent anti-inflammatory activities" (Silva et al., 2003, J. Ethnopharmacol. 89(2-3); 277-283), and similar activity has been observed in essential oils from Lavendula angustifolia Mill. (Hajhashemi et al., 2003, J. Ethnopharmacol. 89(1):67-71). Essential oils have been demonstrated to exhibit antibacterial (Bozic et al., 2003, Phytother. Res. 17(9:1037-1040; Goren et al., 2003, Z. Naturforsch. 58(9-10):687-690; de Abreu Gonzaga et al., 2003, Planta Med. 69(8:773-775; Valero and Salmera, 2003, Int. J. Food Microbial. 85(1-2): 73-81) and antifungal (Paranagama et al., 2003, Lett. Appl. Microbiol. 37(0:86-90; Shin, 2003, Arch. Pharm. Res. 26(5):389-393; Velluti et al., 2003, Int. J. Food Microbiol. 89:145-154) activities. Virucidal activity of essential oils has also been observed, including direct virucidal effects against Herpes simplex viruses types 1 and 2 (Garcia et al., Phytother. Res. 17(9): 1073-1075; Minami et al., 2003, Microbial Immunol. 47(a): 681-684; Schuhmacher et al., 2003, Phytomedicine 10:504-510).

United States Patent Application Publication No. 20050048139 by Modak et al., published Mar. 3, 2005, relates to topical compositions comprising an emollient solvent and an essential oil, which may further comprise additional additives, among which citric acid, glycolic acid and lactic acid are cited.

United States Patent Application Publication No. 20050019431 by Modak et al., published Jan. 27, 2005, relates to compositions comprising a quaternary ammonium compound and an essential oil (or active component thereof).

A number of patent applications relate to compositions comprising an essential oil (or component thereof) where zinc salts are added to inhibit irritation associated with essential oils. Examples of such patent applications include United States Patent Application Publication No. 20040102429 by Modak et al., published May 27, 2004 and United States Patent Application Publication No. 20050238602 by Modak et al., published Oct. 27, 2005, now U.S. Pat. No. 7,435,429.

U.S. Pat. No. 6,858,317 by Aamodt et al., issued Feb. 22, 2005, relates to methods for protecting wood from mold and sap staining fungi which employ a non-toxic mold inhibitor which may be a plant extract such as an essential oil.

U.S. Pat. No. 5,100,652 by Kross et al., issued Mar. 31, 1992, relates to low concentration chlorous-acid generating oral hygiene compositions which may comprise an essential oil as a flavoring agent.

U.S. Pat. No. 5,310,546 by Douglas, issued May 10, 1994, relates to a mouth rinse preparation comprising hydrogen peroxide, zinc chloride, sodium citrate, sodium lauryl sulfate, citric acid and ethanol and optionally an essential oil which is a denaturing agent.

BiON offers several skin care products comprising citric acid, botanicals, and other agents for topical use (San Diego, Calif., US).

Johnson et al. (U.S. Pat. No. 6,319,958 and US20020165130) relates to the use of sesquiterpenoids to promote uptake of exogenous antimicrobial compounds. Similarly, a related article discloses the use of sesquiterpenoids, such as nerolidol, farnesol, bisabolol and apritone, in enhancing bacterial permeability and susceptibility to exogenous antimicrobial compounds, suggesting that sesquiterpenoids have a non-specific and general effect (Brehm-Stecher et al. 2003, Antimicrobial Agents and Chemotherapy, 47(10):3357-3360). In particular, Brehm-Stecher et al. report that nerolidol, farnesol, bisabolol and apritone enhanced the susceptibility of S. aureus to the antibiotics erythromycin, gentamicin, vancomycin, ciproflaxin, clindamycin, and tetracycline.

U.S. Pat. No. 4,867,898 by Spaulding et al., issued Sep. 19, 1989, relates to a liquid hard surface cleaner comprising pine oil and organic, oil-soluble acids at a pH from 0-6.

U.S. Pat. No. 6,753,305 by Raso and Caselli, issued Jun. 22, 2004, relates to a hard surface disinfectant comprising up to 20 percent of cinnamon oil or a component thereof, 0.01-5 percent of an organic acid, and optionally an additional essential oil.

International Patent Application Publication No. WO2007/077573 by Mukhopadhyay, published Jul. 12, 2007, relates to antimicrobial compositions comprising an antimicrobial agent, such as triclosan, and a functionalized hydrocarbon, where the functionalized hydrocarbon can be an essential oil, and/or a solvent.

Infection continues to be the major problem in the management of patients with burn wounds, decubitus ulcers and other surface infections. Control of skin infections is most important in preventing bacteremia and enhancing wound healing. Topical creams containing silver sulfadiazine and other topical antimicrobial agents have been developed and widely used for such purposes. However, complete control of target infection has not been achieved with the use of these agents.

1% silver sulfadiazine (Silvadene®) cream has been effectively used as a prophylactic cream to control burn wound infections. However, it is not very effective in treating established deep wound infections due to the drug's failure to penetrate the wound eschar. The incidence of wound colonization with *S. aureus* or *C. albicans* in Silvadene® treated patients has spurred research for other agents.

It has been well established that continuous control of infection facilitates rapid healing of partial thickness burns, decubitus ulcers and other types of surgical wounds and facilitates their closure. Wound healing, especially in burns, is a complex process for which zinc has been found essential. Studies on zinc have shown beneficial results in wound healing with acceleration of the re-epithelialization process and an antibacterial effect. Zinc oxide has been reported to activate endogenous zinc-dependent matrix metalloproteinases, augment expression of endogenous growth factors and facilitate keratinocyte migration.

In earlier studies, topical treatment of burn wounds with zinc sulfadiazine was found to accelerate wound healing better than treatment with silver sulfadiazine. (Gyn and Obstet, 142:553-559 (1976)).

To prevent or reduce infection of burn wounds, topical ointments have been used. These ointments have incorporated silver sulfadiazine (U.S. Pat. No. 3,761,590, incorporated herein by reference) or various antibiotics. A topical ointment for burns has also been reported which contains a combination of silver salts and norfloxocin, a quinoline antibiotic, or its salts (U.S. Pat. No. 4,404,197, incorporated hereby by reference). In the case where the antibiotic is silver norfloxocin, U.S. Pat. No. 4,404,197 reports a synergistic enhancement of activity. U.S. Pat. No. 5,374,432 relates to topical anti-infective ointments containing an antibiotic, silver salt, and sterile carrier. These compositions were found to not only provide improved antimicrobial efficacy, but also reduced incidence of microbial resistance.

U.S. Pat. No. 6,987,133 relates to a topical preparation containing silver sulfadiazine dispersed or solubilized in a cream or lotion base matrix which can be sprayed directly on the burn wound. European Patent No. EP0653214 relates to a topical antibacterial preparation containing silver sulfadiazine and collagen for the treatment of infected hands and for the advancement of their healing.

There is a continuing desire for an antimicrobial or wound healing composition that are non-irritating, safe, and effective for repeated use in various professional and non-professional settings.

3. SUMMARY

Disclosed are compositions comprising antimicrobially effective low concentrations of benzyl alcohol, one or more essential oil and one or more botanical extract. In certain embodiments, compositions are provided having antimicrobial active agents that are substantially or essentially entirely derived from natural sources, thereby allowing the user to avoid harsh and/or toxic chemicals. This may be particularly advantageous in products for use by or on children or pets or for use in households or other environments occupied by children or animals.

In certain embodiments, an antimicrobial composition is provided comprising benzyl alcohol (from about 0.1% (w/w) to about 10% (w/w)), one or more essential oil such as but not limited to lemongrass oil, cinnamon oil, thyme oil, galanga oil, orange oil, pomegranate oil, curry leaf oil and combinations thereof (from about 0.02% (w/w) to about 1.0% (w/w)), and one or more botanical extract such as wasabi extract, grapefruit seed extract, honey suckle extract, cedarwood extract, pomegranate extract, Echinacea extract, aspen bark extract, willow bark extract, citrus extract, Brahmi extract and combinations there of (from about 0.1% (w/w)-1.0% (w/w)). Optional ingredients include one or more sesquiterpenoid such as farnesol, nerolidol, bisabolol, apritone, citral and combinations thereof (from about 0.03% (w/w) to about 2% (w/w)), one or more plant derived alcohol (from about 5% (w/w) to about 20% (w/w)), one or more natural organic acid such as a fruit acid, benzoic acid, salicylic acid and combinations thereof (from about 0.02% (w/w) to about 2.0% (w/w)), and vegetable glycerin.

"About" as used herein means ±20% of the recited value.

All ranges herein include the recited values.

In certain non-limiting embodiments, an antimicrobial composition is provided comprising:

(a) from about 0.5% (w/w) to about 50% (w/w) benzyl alcohol;

(b) from about 0.01% (w/w) to about 5% (w/w) essential oil; and (e) from about 0.1% (w/w) to about 4% (w/w) sesquiterpenoid, wherein the composition does not comprise an alkanediol.

In certain non-limiting embodiments, an antimicrobial composition is provided comprising:

(a) from about 0.5% (w/w) to about 50% (w/w) benzyl alcohol;

(b) from about 0.01% (w/w) to about 5% (w/w) essential oil; and (c) from about 0.5% (w/w) to about 10% (w/w) botanical extract selected from the group consisting of wasabi extract, honeysuckle extract, cedar wood extract, aspen bark extract, willow bark extract, tobacco extract, and combinations thereof.

In certain non-limiting embodiments, an antimicrobial composition is provided comprising:

(a) from about 0.5% (w/w) to about 50% (w/w) benzyl alcohol;

(b) from about 0.01% (w/w) to about 5% (w/w) essential oil;

(c) from about 0.5% (w/w) to about 10% (w/w) botanical extract;

(d) from about 0 to about 20% (w/w) fruit acid; and (e) from about 0.1% (w/w) to about 4% (w/w) sesquiterpenoid, wherein the composition does not comprise an alkanediol.

In certain non-limiting embodiments, an antimicrobial composition is provided comprising (a) from about 0.5% (w/w) to about 2.0% (w/w) benzyl alcohol;

(b) from about 0.5% (w/w) to about 4.0% (w/w) incroquat;

(c) from about 0.2% (w/w) to about 0.5% (w/w) benzoic acid;

(d) from about 0.05% (w/w) to about 1% (w/w) of one or more essential oil selected from the group consisting of oregano oil, thymol, rosemary oil, cinnamon oil (e.g., cinnamon leaf oil or cinnamon bark oil), galangal oil, pomegranate oil, and lemongrass oil; and (e) from about 0.2% (w/w) to about 2.0% (w/w) of one or more botanical selected from the group consisting of wasabi extract, grapefruit extract, citrus extract, honeysuckle extract, aloe gel, and aloe leaf juice. In certain subsets of this embodiment, the composition further comprises from about 0.1% (w/w) to about 0.5% (w/w) zinc oxide. In certain subsets of this embodiment, the composition further comprises from about 0.2% (w/w) to about 0.5% sodium benzoate. In certain subsets of this embodiment, the composition further comprises from about 0.1% (w/w) to about 1.0% (w/w) pentanediol. In certain subsets of this embodiment, the composition further comprises grapefruit seed or another citrus extract, for example, at a concentration from about 0.3% (w/w) to about 1.0% (w/w). In certain subsets of this embodiment, the composition further comprises one or more of Vitamin E and/or Vitamin C, for example with each being at a concentration from about 0.02% (w/w) to about 0.2% (w/w). In certain subsets of this embodiment, the composition further comprises a sesquiterpenoid or a mixture of sesquiterpenoids, for example at a concentration from about 0.3% (w/w) to about 2.0% (w/w). In certain subsets of this embodiment, the composition does not comprise an antibiotic or antiseptic agent which is a biguanide, a chlorinated phenol, or a quaternary ammonium compound. In certain subsets of this embodiment, the composition does not comprise phenylethanol. In certain subsets of this embodiment, the composition does not comprise phenoxyethanol. In certain subsets of this embodiment, the composition does not comprise polymixin, miconazole, fluconazole, itriconazole, or keoconazole. In certain subsets of this embodiment, the composition does not comprise neomycin. In certain subsets of this embodiment, the composition does not comprise bacitracin. In certain subsets of this embodiment, the composition does not comprise povidone iodine or other iodine-containing compounds.

In certain non-limiting embodiments, an antimicrobial composition is provided comprising (a) from about 0.1% (w/w) to about 2.0% (w/w) benzyl alcohol;

(b) from about 0.1% (w/w) to about 2.0% (w/w) benzoic acid;

(c) from about 0.5% (w/w) to about 1.0% (w/w) phenoxyethanol;

(d) from about 0.3% (w/w) to about 1.3% (w/w) sesquiterpenoid(s) in the form of a single sesquiterpenoid or a mixture of sesquiterpenoids;

(e) from about 0.05% (w/w) to about 2.5% (w/w) of one or more essential oil selected from the group consisting of oregano oil, thymol, rosemary oil, cinnamon oil (e.g., cinnamon leaf oil or cinnamon bark oil), galangal oil, pomegranate oil, and lemongrass oil; and (f) from about 0.2% (w/w) to about 2.0% (w/w) of one or more botanical selected from the group consisting of wasabi extract, grapefruit extract, citrus extract, honeysuckle extract, aloe gel, and aloe leaf juice. In certain subsets of this embodiment, the composition further comprises from about 0.5% (w/w) to about 3.0% (w/w) pentylene glycol. In certain subsets of this embodiment, the composition further comprises from about 0.5% (w/w) to about 2.0% (w/w) of a cationic surfactant. In certain subsets of this embodiment, the composition does not comprise an antibiotic or antiseptic agent which is a biguanide, a chlorinated phenol, or a quaternary ammonium compound. In certain subsets of this embodiment, the composition does not comprise phenylethanol. In certain subsets of this embodiment, the composition does not comprise polymixin, miconazole, fluconazole, itriconazole, or keoconazole. In certain subsets of this embodiment, the composition does not comprise neomycin. In certain subsets of this embodiment, the composition does not comprise bacitracin. In certain subsets of this embodiment, the composition does not comprise povidone iodine or other iodine-containing compounds.

In certain non-limiting embodiments, an antimicrobial composition is provided comprising (a) from about 0.1% (w/w) to about 2.0% (w/w) benzyl alcohol;

(b) from about 0.02% (w/w) to about 2.0% (w/w) benzoic acid;

(c) from about 0.1% (w/w) to about 1.0% (w/w) phenylethanol;

(d) from about 0.02% (w/w) to about 1% (w/w) sesquiterpenoid(s) in the form of a single sesquiterpenoid or a mixture of sesquiterpenoids;

(e) from about 0.05% (w/w) to about 2.5% (w/w) of one or more essential oil selected from the group consisting of oregano oil, thymol, rosemary oil, cinnamon oil (e.g., cinnamon leaf oil or cinnamon bark oil), galangal oil, pomegranate oil, and lemongrass oil; and (f) from about 0.05% (w/w) to about 2.0% (w/w) of one or more botanical selected from the group consisting of wasabi extract, grapefruit extract, citrus extract, honeysuckle extract, aloe gel, and aloe leaf juice. In certain subsets of this embodiment, the composition does not comprise an antibiotic or antiseptic agent which is a biguanide, a chlorinated phenol, or a quaternary ammonium compound. In certain subsets of this embodiment, the composition does not comprise phenoxyethanol. In certain subsets of this embodiment, the composition does not comprise polymixin, miconazole, fluconazole, itriconazole, or keoconazole. In certain subsets of this embodiment, the composition does not comprise neomycin. In certain subsets of this embodiment, the composition does not comprise bacitracin. In certain subsets of this embodiment, the composition does not comprise povidone iodine or other iodine-containing compounds.

In certain non-limiting embodiments, a disinfectant is provided comprising (a) from about 0.5% (w/w) to about 3.0% (w/w) benzyl alcohol;

(b) from about 0.05% (w/w) to about 2.5% (w/w) of lemongrass oil, orange oil, or a combination thereof;

(c) from about 0.1% (w/w) to about 2.0% (w/w) of fruit acid; and (d) from about 0.1% (w/w) to about 2.0% (w/w) of a botanical selected from the group consisting of wasabi extract and honeysuckle extract.

In certain non-limiting embodiments, a wound-healing composition is provided comprising (a) from about 0.1% (w/w) to about 0.5% (w/w) benzyl alcohol;

(b) from about 0.2% (w/w) to about 1.0% (w/w) zinc oxide;

(c) from about 0.05% (w/w) to about 0.7% (w/w) curcumin; and (d) from about 0.1% (w/w) to about 1.0% (w/w) of each of at least two of the following: pomegranate oil, rosemary oil, lemongrass oil, cinnamon oil (e.g., cinnamon leaf oil or cinnamon bark oil), thymol, and buckthorn oil.

In certain non-limiting embodiments, a surface disinfectant is provided comprising:

(a) from about 1.0% (w/w) to about 30% (w/w) benzyl alcohol;

(b) from about 0.1% (w/w) to about 4.0% (w/w) of a mixture of pine oil and an essential oil selected from the group consisting of lemongrass oil, orange oil, cinnamon leaf oil, cinnamon bark oil and a combination thereof;

(c) from about 2% (w/w) to about 10% (w/w) fruit acid;

(d) from about 5% (w/w) to about 25% (w/w) surfactant; and (e) water, optionally further comprising between about 3% (w/w) and about 50% (w/w) aliphatic alcohol (for example, but not limited to, a mixture of aliphatic alcohols, for example mixtures of ethanol and propanol or butanol, e.g., SDA 3C or SDA 40B)

In certain non-limiting embodiments, a surface disinfectant is provided comprising:
from about 2.5% (w/w) to about 10% (w/w) of an essential oil selected from the group consisting of lemongrass oil, orange oil, cinnamon oil, and a combination thereof;
from about 0.5% (w/w) to about 5.0% (w/w) pine oil;
from about 25% (w/w) to about 50% (w/w) surfactant;
from about 10% (w/w) to about 20% (w/w) fruit acid;
from about 20% (w/w) to about 40% (w/w) aliphatic alcohol; and
water.

In certain non-limiting embodiments, a cleaning composition is provided comprising from about 1% (w/w) to about 5% (w/w) lemongrass oil, from about 0.1% (w/w) to about 1% (w/w) pine oil, and from about 5% (w/w) to about 20% (w/w) citric acid.

In various non-limiting embodiments, the compositions may be utilized in personal care products such as soaps, scrubs, cosmetics, topical creams and lotions, wound care products, burn wound cream, decubitous ulcer cream (with anti-inflammatory botanicals and the use of silver sulfadiazene as an anti-microbial agent), rapidly acting skin disinfectants, disinfecting wipes, and veterinary products, such as antimicrobial lotion for mastitis, teat dip, and therapeutic ointments. The compositions of the application may be used in concentrations from about 1% to about 10% in personal care products or topical creams. In other non-limiting embodiments, the compositions may be utilized in household and industrial applications, for example as surface disinfectants, surface cleaners, pesticides and preservatives.

4. DETAILED DESCRIPTION

For clarity of description, and not by way of limitation, the detailed description of the application is divided into the following subsections:
(4.1) benzyl alcohol;
(4.2) essential oils;
(4.3) botanical extracts;
(4.4) Sesquiterpenoids;
(4.5) alkanediols;
(4.6) solvents;
(4.7) natural organic acids;
(4.8) personal care products;
(4.9) wound healing;
(4.10) veterinary products;
(4.11) household/industrial products;
(4.12) medical devices; and
(4.13) pesticides.

4.1 Benzyl Alcohol

The compositions disclosed herein comprise benzyl alcohol, at a concentration (percent weight/weight, "% w/w") from about 0.05% (w/w) to about 60% w/w, or from about 0.5% (w/w) to about 50% (w/w), or from about 0.5% (w/w) to about 50% (w/w); or from about 0.5% (w/w) to about 2.0% (w/w), or from about 0.1% (w/w) to about 2.0% (w/w), or from about 0.1% (w/w) to about 0.5% (w/w), or from about 0.5% (w/w) to about 5% (w/w), or from about 5.0% (w/w) to about 20% (w/w), including but not limited to about 0.05% (w/w), 0.1% (w/w) 0.5% (w/w), 1.0% (w/w), 2.0% (w/w), 3.0% (w/w), 4.0% (w/w), 5.0% (w/w), 6.0% (w/w), 7.0% (w/w), 8.0% (w/w), 9.0% (w/w), 10.0% (w/w), 12% (w/w), 15% (w/w), 18% (w/w), 20% (w/w), 25% (w/w), 30% (w/w), 35% (w/w), 40% (w/w), 45% (w/w), 50% (w/w), 55% (w/w), and 60% (w/w).

In certain, non-limiting embodiments, the compositions disclosed herein comprise benzyl alcohol, at a concentration of between about 0.1 and about 0.5% w/w; or between about 0.1 and about 0.45 w/w; or between about 0.1 and about 0.4% w/w; or between about 0.1 and about 0.35% w/w; or between about 0.1 and about 0.3% w/w; or between about 0.1 and about 0.25% w/w; or between about 0.1 and about 0.2% w/w; or between about 0.1 and about 0.15% w/w.

Benzyl alcohol for use in the compositions disclosed herein may be produced synthetically or may be obtained from one or more natural plant (botanical) source.

4.2 Essential Oils

Essential oils ("EOs"), as defined herein, are volatile oils obtained from plant or animal sources, or their synthetic equivalents, and are composed of complex mixtures of several constituents such as monoterpenes and sesquiterpene hydrocarbons, monoterpene and sesquiterpene alcohols, esters, ethers, aldehydes, ketones, oxides and the like. Examples of EOs include, but are not limited to, cinnamon oil (e.g., cinnamon leaf oil or cinnamon bark oil), basil oil, bergamot oil, clary sage oil, ylang-ylang oil, neroli oil, sandalwood oil, frankincense oil, ginger oil, peppermint oil, lavender oil, jasmine absolute, geranium oil bourbon, spearmint oil, clove oil, patchouli oil, rosemary oil, rosewood oil, sandalwood oil, tea tree oil, vanilla oil, lemongrass oil, oregano oil, thymol, galangal oil, cedar wood oil, balsam oils, tangerine oil, Hinoki oil, Hiba oil, ginko oil, eucalyptus oil, lemon oil, orange oil, sweet orange oil, pomegranate seed oil, pomegranate oil, manuka oil, citronella oil, curry leaf oil, and calendula oil.

Individual constituents ("ICs") of essential oils may be isolated from the oil (natural) or may be entirely or partially chemically synthetic, and include, but are not limited to, thyme, oregano, curcumin, l-citronellol, α-amylcinnamaldehyde, lyral, geraniol, farnesol, hydroxycitronellal, isoeugenol, eugenol, camphor, eucalyptol, linalool, citral, thymol, limonene and menthol. Further examples of ICs include sesquiterpenoid compounds, which may be the active compounds in the essential oils. Sesquiterpenoid compounds, containing 15 carbons, are formed biosynthetically from three 5-carbon isoprene units. Sesquiterpenoid compounds include, but are not limited to, farnesol, nerolidol, bisabolol, apritone, chamazulene, santalol, zingiberol, carotol, and caryophyllen.

Mixtures of one or more EO, one or more IC, and one or more EO as well as one or more IC, are encompassed by the present subject matter. In specific non-limiting embodiments of the application, an IC is selected from the (non-limiting) group consisting of camphor, curcumin, alpha-pinene, constituents of cinnamon leaf oil such as, cinnamaldehyde, cinnamylacetic ester, cinnamic acid, ethyl cinnamate, methyl chavicol, linalool, beta-caryophyllene, and eugenol; constituents of lemongrass oil such as d-limonene, geranyl acetate, nerol, geraniol, citral, and/or myrcene; constituents of citronella oil such as geraniol, citronellol, citronellal, geranyl acetate, limonene, methyl isoueugenol, and/or elemol; components of basil oil such as camphor, limonene, and/or β-selinene; and constituents of orange oil such as α-pinene, sabinene, myrcene, limonene, linalool, citronellal, neral and/or geranial. An EO or IC for use in the application may be obtained from its natural source or may be chemically synthesized.

In preferred non-limiting embodiments of the application, the EO is selected from one or more EO from the group consisting of cinnamon oil (CO) (bark or leaf), lemongrass oil (LGO), and basil oil (BO), all of which have little to no fragrance, or nonfragrant oils such as pomegranate seed oil (PSO).

Calendula contains high amounts of flavonoids, plant-based antioxidants that protect the body against cell-damaging free radicals. It appears to have anti-inflammatory, antiviral, and antibacterial effects. Animal studies show that calendula accelerates wound healing, possibly by increasing blood flow to the wounded area and by helping the body produce collagen proteins, which are used to heal skin and connective tissue.

4.3 Botanical Extracts

Botanical extracts, as defined herein, include plant, herbal, and fruit extracts, which are not "essential oils" as noted above. The botanical extracts utilized herein include but are not limited to wasabi, honeysuckle, cedar wood, aspen bark, willow bark, Brahmi (*Bacopa monnieri*) extract, citrus extract *Camellia sinensis* (green tea), grapes, pomegranate, Echinacea, *Centella Asiatica*, Elderflower, Irish moss, Mallow, soap bark, Yucca, Clary sage, oregano, thyme, curcumin compounds, resveratrol (polyphenolic compound from grape, berries, etc.) vetivert and mixtures thereof. The botanical utilized to obtain the botanical extract may be obtained from any of the plant parts including the leaves, pulp, seeds, or stems, fruit and fruit seeds, as well as the whole plant. Herbal extracts can be, for example, standardized extracts that are dispersible and/or soluble in aqueous medium.

Examples of herbal extracts include, without limitation, extracts of chamomile, rosemary, aloe, nettle, *Centella asiatica, ginkgo biloba*, betula, and witch hazel. Such extracts may be delivered in a carrier such as water, propylene glycol, hydroalcohol, glycerine, or butylene glycol. Additional extracts with nutritional quality can be used, including, without limitation, green tea, white tea, grape skin, grape seed, resveratrol grapefruit, grapefruit seed, grapefruit peel, citrus fruits (other than grapefruit extract) bilberry, blueberry, *Ginkgo biloba*, soy isoflavones, soy extract, fermented soy protein, black cohosh, St. John's wort, echinacea, chamomile, rosemary, aloe extract and juice, nettle, coconut fruit and *Centella asiatica*. Botanical extracts can be obtained from, for example, Active Organics (Lewisville, Tex.), New Age Botanicals (Garland, Tex.), Triarco Industries (Wayne, N.J.), and Aloecorp (Broomfield, Colo.).

Examples of nonfragrant botanicals include pomegranate seed oil (PSO), mixtures of edible plant extract Kefiprotect (KP), and tetrahydrocurcuminoid (THC). Turmeric and curcuminoids have been documented to have anti inflammatory, antioxidant and wound healing properties. The following curcuminoids can be used in topical creams, tetrahydrocurcumin, tetrahydrodemethoxycurcumin, tetrahydrobisdemethoxycurcumin, and mixtures thereof. Additional examples of botanical extracts include coconut derived phospholipid (Arlasik phospholipid PTM), natural blends of fatty acids which mimic those found in the stratum corneum, mixture of fatty acids with pigments such as carotenes, carotenoids or phytosterols that are known to facilitate repair to damaged skin, and the like. Specific examples of useful botanical extracts include avocado, which contains the sterol sitosterol; carrot, which contains beta carotene; sesame oil which contains a mixture of saturated and unsaturated fatty acids, and brazil nut oil. Because of its broad distribution of fatty acids, extracts such as brazil nut oil, can outperform single fatty acids with respect to incorporation into the lipid lamellar structures. Brazil nut oil (BNO) originates from the harvested fruit from the South American rain forest tree: *Bertholletia excelsa.*

Botanical extracts also include flavonoids and terpenoids. The flavonoids contemplated by the present subject matter include, but are not limited to, turin, quercetin, hesperidin, and naringin. Terpenoids contemplated by the present subject matter include, but are not limited to, monoterpenes, sesquiterpenes, and diterpenes.

In preferred non-limiting embodiments of the application, the botanical extract is selected from one or more extract selected from the group consisting of grapefruit seed extract (GSE), pomegranate seed oil (PSO), citrus fruit extract, or mixtures of edible plant extract Kefiprotect (KP), coconut derived phospholipid (Arlasik phospholipid PTM), and tetrahydrocurcuminoid (THC).

4.4 Sesquiterpenoids

Compositions disclosed herein comprise one or more sesquiterpenoid selected from the group consisting of farnesol, nerolidol, bisabolol, apritone, citral and combinations thereof.

4.5 Alkanediols

In non-limiting embodiments, bifunctional alcohols which may be used according to the present subject matter are alkanediols. Suitable alkanediols include, but are not limited to, propanediol, butanediol, dodecanediol, decanediol, nonanediol, octanediol, heptanediol, hexanediol, and pentanediol.

In particular non-limiting embodiments, the alkanediols have a carbon backbone of between 3 and 25 carbon atoms, including but not limited to 1,9 Nonanediol, 1,2-Decanediol, 1,10-Decanediol, 1,11-Undecanediol, 1,2-Dodecanediol, 1,12 Dodecanediol, Cyclododecanediol, 1,13-Tridecanediol, 1,2-Tetradecanediol, 1,14-Tetradecanediol, 1,15-Pentadecanediol, 1,16-Hexadecanediol, 1,17-Heptadecanediol, 1,18-Octadecanediol, 1,19-Nonadecanediol, 1,20-Eicosanediol, 1,21-Heneicosanediol, 1,22-Docosanediol, 1,23-Tricosanediol, 1,24-Tetracosanediol, 1,25-Pentacosanediol.

In certain embodiments an alkanediol is obtained from a natural product. In certain embodiments an alkanediol is chemically synthesized.

4.6 Solvents

In various non-limiting embodiments, the compositions of the present subject matter may include one or more solvent, including but not limited to solvent(s) selected from the group consisting of water, alcohols, plant derived alcohols, glycols, glycerol, glycerine, octoxyglycerin, diglycerol, propylene glycol, dipropylene glycol, and vegetable oils.

Preferred but non-limiting examples of non-alkanediol alcohols for solubilization are aliphatic alcohols having between about 1 and 8 carbon atoms such as methanol, ethanol, n-propanol, isopropyl alcohol, 2-methyl-2 propanol, hexanol, or combinations thereof. Aromatic alcohols, for example, but not by way of limitation, phenoxyethanol, benzyl alcohol, 1-phenoxy-2-propanol, and/or phenethyl alcohol, may also optionally be used in combination with aliphatic alcohols.

Aromatic alcohols, for example, but not by way of limitation, include phenoxyethanol, benzyl alcohol, 1-phenoxy-2-propanol, and/or phenethyl alcohol, for example at a concentration of between about 0.5 and 5% (weight/weight) may also optionally be used in combination with aliphatic alcohols. A further solvent which optionally may be comprised in a composition of the application is isopropyl myristate. Additional aliphatic alcohols include ethanol, denatured alcohol (SDA 40B and SDA 3C) and isopropanol.

Compositions comprising combinations of benzyl alcohol, botanicals, and 1,3 propanediol and its derivatives such as 2-methyl-1-nitro 1,3-propanediol (Diol) or 2-Hydroxymethyl 2-nitro 1,3-propanediol (Triol), may further contain cosolvents such as glycerin, octoxyglycerin, alcohol, glycols, butanediol, and phenoxy ethanol.

In preferred non-limiting embodiments, the solvent is benzyl alcohol, glycerin, or a combination thereof.

In certain embodiments, the solvents are used at concentrations ranging from about 0.001% to about 90% (w/w), or from about 1% to about 85% (w/w), or from about 10% to about 70% (w/w), or from about 30% to about 65% (w/w). In alternative embodiments, the concentration ranges range from about 5% to about 90% (w/w), preferably from about 30% to about 90% (w/w), and more preferably from about 40% to about 80% (w/w). In a preferred embodiment, the solvent is a natural product, for example, benzyl alcohol derived from the *Cassia* plant.

In alternative preferred non-limiting embodiments of the application, the solvent is benzyl alcohol or its derivatives, e.g., hydroxylbenzyl alcohol, nitro benzyl alcohol, or other derivatives. Benzyl alcohol concentrations ranging from about 0.5% to about 10% (w/w), preferably from about 0.5% to about 5% (w/w), more preferably from about 0.5% to about 4% (w/w), have been found to exhibit antimicrobial efficacy with certain botanical organic acids, and in particular fruit acids. Alternative embodiments use from about 1.0% to about 5.0% (w/w), or from about 1% to about 3% (w/w) benzyl alcohol. Use of other botanicals and synthetic antimicrobials along with benzyl alcohol and these acids further enhances the activity as discussed in further detail below.

4.7 Natural Organic Acids

Natural organic acids, such as fruit acids, which may be used according to the application include but are not limited to fruit acid, citric acid, glycolic acid, lactic acid, malic acid, tartaric acid, benzoic acid, salicylic acid, and acetic acid. In certain non-limiting embodiments, the fruit acid is Multifruit BSC (Arch Chemicals), which is a mixture of lactic, citric, tartaric, glycolic, and malic acid extracted from plants. In preferred non-limiting embodiments, the fruit acid is lactic acid. A fruit acid for use in the application may be obtained from its natural source or may be chemically synthesized.

Other organic acids which may be used in compositions disclosed herein include but are not limited to benzoic acid and its derivatives including salt forms, for example, a benzyl benzoate, paramino benzoic acid, nitro benzoic acid, hydroxyl benzoic acid, fluorobenzoic acid, and benzyl salicylate.

Fruit acids may be used according to the application to assist in the controlled release of the silver compound. Non-limiting examples of fruit acids include but are not limited to citric acid, glycolic acid, lactic acid, malic acid, tartaric acid and acetic acid. In certain non-limiting embodiments, the fruit acid is Multifruit BSC (Arch Chemicals), which is a mixture of lactic, citric, tartaric, glycolic, and malic acid extracted from plants. A fruit acid for use in the compositions of the present subject matter may be obtained from its natural source or may be chemically synthesized. In preferred non-limiting embodiments of the application, the fruit acid is lactic acid or citric acid.

In non-limiting embodiments, concentrations of fruit acids ranges from about 0% to about 70% (w/w), or from about 5% to about 70% (w/w), or from about 5% to about 20% (w/w), or from about 10% to about 20% (w/w). In alternative non-limiting embodiments of the application, the concentrations range from about 0% to about 20% (w/w), or from about 0% to about 40% (w/w), or from about 0.1% to about 20% (w/w), or from about 0.2% to about 4% (w/w), or from about 0.5% to about 4% (w/w), or from about 2% to about 4% (w/w).

In alternative embodiments, the concentrations of natural organic acid present in a composition for use range from about 0.2% to about 2% (w/w), or from about 0.2 to about 1% (w/w). In another alternative embodiments, the natural organic acids are present in a composition for use at concentrations ranging from between about 0.01% to about 5% (w/w), or from about 0.01% to about 4% (w/w), or from about 0.01% to about 3% (w/w), or from about 0.01% to about 2% (w/w), or from about 0.01% to about 1% (w/w), or from about 0.02% to about 5% (w/w), or from about 0.02% to about 4% (w/w), or from about 0.02% to about 3% (w/w), or from about 0.02% to about 2% (w/w), or from about 0.02% to about 1% (w/w), or from about 0.05% to about 2.0% (w/w), or from about 0.1% to about 2.0% (w/w).

4.8 Personal Care Products

In non-limiting embodiments, personal care product compositions are provided, comprising benzyl alcohol and one or more essential oil and/or one or more botanical extract, for example a plant or fruit extract. Preferably, the pH of personal care products is between about 3.0 and 6.0.

Non-limiting examples of personal care products which may utilize the compositions of the present subject matter include bar soap, liquid soap (e.g., hand soap), hand sanitizer (including rinse off and leave-on alcohol based and aqueous-based hand disinfectants), preoperative skin disinfectant, cleansing wipes, disinfecting wipes, body wash, acne treatment products, antifungal diaper rash cream, antifungal skin cream, shampoo, conditioner, cosmetics (including but not limited to liquid or powder foundation, liquid or solid eyeliner, mascara, cream eye shadow, tinted powder, "pancake" type powder to be used dry or moistened, etc.) deodorant, antimicrobial creams, body lotion, hand cream, topical cream, aftershave lotion, skin toner, mouth wash, toothpaste, sunscreen lotion, and baby products such as, but not limited to, cleansing wipes, baby shampoo, baby soap, and diaper cream. The present subject matter may also be applied to wound care items, such as, but not limited to, wound healing ointments, creams, and lotions, wound coverings, burn wound cream, bandages, tape, and steri-strips, and medical articles such as medical gowns, caps, face masks, and shoe-covers, surgical drops, etc. Additional products include but are not limited to oral products such as mouth rinse, toothpaste, and dental floss coatings, veterinary and pet care products, preservative compositions, and surface disinfectants including solutions, sprays or wipes.

Personal care compositions provided herein may further comprise one or (preferably) more than one component selected from the group consisting of emollients, stabilizing agents, thickening agents, humectants, anti-inflammatory agents, antimicrobial agents, neutralizing agents, surfactants, water, silicone polymers, alcohols, and hydrogels, as well as additional components as may be known in the art. Non-limiting examples of such components are set forth below.

In various non-limiting embodiments, a personal care product may comprise an emollient, for example PEG 20 almond glycerides, Probutyl DB-10, Glucam P-20, Glucam E-10, Glucam P-10, Glucam E-20, Glucam P-20 distearate, glycerin, propylene glycol, octoxyglycerin, cetyl acetate, acetylated lanolin alcohol (e.g., Acetulan), cetyl ether (e.g., PPG-10), myristyril ether (e.g., PPG-3), hydroxylated milk glycerides (e.g., Cremeral HMG), polyquaternium compounds (e.g., U-care compounds), copolymers of dimethyl dialyl ammonium chloride and acrylic acid (e.g., Merquat), dipropylene glycol methyl ethers (e.g., Dowanol DPM, Dow Corning), polypropylene glycol ethers (e.g., Ucon 50-HB-600, Union Carbide) and silicon polymers. Other suitable emollients may include hydrocarbon-based emollients such as petrolatum or mineral oil, fatty ester-based emollients, such as methyl, isopropyl and butyl esters of fatty acids such as isopropyl palmitate, isopropyl myristate, isopropyl isostearate, isostearyl isostearate, diisopropyl sebacate, and propylene dipelargonate, 2-ethylhexyl isononoate, 2-ethylhexyl stearate, $C_{12}$-$C_{16}$ fatty alcohol lactates such as cetyl lactate and lauryl lactate, isopropyl lanolate, 2-ethylhexyl salicylate, cetyl myristate, oleyl myristate, oleyl stearate, oleyl oleate, hexyl laurate, and isohexyl laurate. Additional useful emollients include lanolin, olive oil, cocoa butter, and shea butter.

In various non-limiting embodiments, a personal care product may comprise a stabilizing agent such as an antioxidant, for example but not limited to vitamin C (ascorbic acid) and/or vitamin E (tocopherol), and/or a surfactant, for example but not limited to incromide or silicone-based surfactants (Masil SF-19, BASF).

In various non-limiting embodiments, a personal care product may comprise a thickening and/or gelling agent such as stearyl alcohol, cationic hydroxy ethyl cellulose (Ucare; JR30), hydroxy propyl methyl cellulose, hydroxy propyl cellulose (Klucel), chitosan pyrrolidone carboxylate (Kytamer), behenyl alcohol, zinc stearate, emulsifying waxes, including but not limited to Incroquat and Polawax, an addition polymer of acrylic acid, a resin such as Carbopol® ETD™ 2020, guar gum, acacia, acrylates/steareth-20 methacrylate copolymer, agar, algin, alginic acid, ammonium acrylate co-polymers, ammonium alginate, ammonium chloride, ammonium sulfate, amylopectin, attapulgite, bentonite, C9-15 alcohols, calcium acetate, calcium alginate, calcium carrageenan, calcium chloride, caprylic alcohol, carbomer 910, carbomer 934, carbomer 934P, carbomer 940, carbomer 941, carboxymethyl hydroxyethyl cellulose, carboxymethyl hydroxypropyl guar, carrageenan, cellulose, cellulose gum, cetearyl alcohol, cetyl alcohol, corn starch, damar, dextrin, dibenzlidine sorbitol, ethylene dihydrogenated tallowamide, ethylene diolamide, ethylene distearamide, gelatin, guar gum, guar hydroxypropyltrimonium chloride, hectorite, hyaluronic acid, hydrated silica, hydroxybutyl methylcellulose, hydroxyethylcellulose, hydroxyethyl ethylcellulose, hydroxyethyl stearamide-MIPA, isocetyl alcohol, isostearyl alcohol, karaya gum, kelp, lauryl alcohol, locust bean gum, magnesium aluminium silicate, magnesium silicate, magnesium trisilicate, methoxy PEG-22/dodecyl glycol copolymer, methylcellulose, microcrystalline cellulose, montmorillonite, myristyl alcohol, oat flour, oleyl alcohol, palm kernel alcohol, pectin, PEG-2M, PEG-5M, polyacrylic acid, polyvinyl alcohol, potassium alginate, potassium aluminium polyacrylate, potassium carrageenan, potassium chloride, potassium sulfate, potato starch, propylene glycol alginate, sodium acrylate/vinyl alcohol copolymer, sodium carboxymethyl dextran, sodium carrageenan, sodium cellulose sulfate, sodium chloride, sodium polymethacylate, sodium silicoaluminate, sodium sulfate, stearalkonium bentotnite, stearalkonium hectorite, stearyl alcohol, tallow alcohol, TEA-hydrochloride, tragacanth gum, tridecyl alcohol, tromethamine magnesium aluminium silicate, wheat flour, wheat starch, xanthan gum, abietyl alcohol, acrylinoleic acid, aluminum behenate, aluminum caprylate, aluminum dilinoleate, aluminum salts, such as distearate, and aluminum isostearates, beeswax, behenamide, butadiene/acrylonitrile copolymer, C29-70 acid, calcium behenate, calcium stearate, candelilla wax, carnauba, ceresin, cholesterol, cholesterol hydroxystearate, coconut alcohol, copal, diglyceryl stearate malate, dihydroabietyl alcohol, dimethyl lauramine oleate, dodecanoic acid/cetearyl alcohol/glycol copolymer, erucamide, ethylcellulose, glyceryl triacetyl hydroxystearate, glyceryl tri-acetyl ricinolate, glycol dibehenate, glycol di-octanoate, glycol distearate, hexanediol distearate, hydrogenated C6-14 olefin polymers, hydrogenated castor oil, hydrogenated cottonseed oil, hydrogenated lard, hydrogenated menhaden oil, hydrogenated palm kernel glycerides, hydrogenated palm kernel oil, hydrogenated palm oil, hydrogenated polyisobutene, hydrogenated soybean oil, hydrogenated tallow amide, hydrogenated tallow glyceride, hydrogenated vegetable glyceride, hydrogenated vegetable oil, Japan wax, jojoba wax, lanolin alcohol, shea butter, lauramide, methyl dehydroabietate, methyl hydrogenated rosinate, methyl rosinate, methylstyrene/vinyltoluene copolymer, microcrystalline wax, montan acid wax, montan wax, myristyleicosanol, myristyloctadecanol, octadecene/maleic anhyrdine copolymer, octyldodecyl stearoyl stearate, oleamide, oleostearine, ouricury wax, oxidized polyethylene, ozokerite, paraffin, pentaerythrityl hydrogenated rosinate, pentaerythrityl tetraoctanoate, pentaerythrityl rosinate, pentaerythrityl tetraabietate, pentaerythrityl tetrabehenate, pentaerythrityl tetraoleate, pentaerythrityl tetrastearate, ophthalmic anhydride/ glycerin/glycidyl decanoate copolymer, ophthalmic/ trimellitic/glycols copolymer, polybutene, polybutylene terephthalate, polydipentene, polyethylene, polyisobutene, polyisoprene, polyvinyl butyral, polyvinyl laurate, propylene glycol dicaprylate, propylene glycol dicocoate, propylene glycol diisononanoate, propylene glycol dilaurate, propylene glycol dipelargonate, propylene glycol distearate, propylene glycol diundecanoate, PVP/eiconsene copolymer, PVP/hexadecene copolymer, rice bran wax, stearlkonium bentonite, stearalkonium hectorite, stearamide, stearamide DEA-distearate, stearamide DIBA-stearate, stearamide MEA-stearate, stearone, stearyl erucamide, stearyl stearate, stearyl stearoyl stearate, synthetic beeswax, synthetic wax, trihydroxystearin, triisononanoin, triisostearin, tri-isostearyl trilinoleate, trilaurin, trilinoleic acid, trilinolein, trimyristin, triolein, tripalmitin, tristearin, zinc laurate, zinc myristate, zinc neodecanoate, zinc rosinate, and mixtures thereof. The gelling agents used in vehicles may be natural gelling agents such as natural gums, starches, pectins, agar and gelatin. Often, the gelling agents are based on polysaccharides or proteins Examples include but are not limited to guar gum, Xanthum gum, Alginic acid (E400), sodium alginate (E401), potassium alginate (E402), ammonium alginate (E403 alkanediol, may further comprise a humectant, such as, for example, glycerin, 1-2-propylene glycol, dipropylene glycol, polyethylene glycol, 1,3-butylene glycol, or 1,2,6-hexanetriol.

In certain non-limiting, one or more additional antimicrobial agent may be comprised, for example, where such antimicrobial agent may be selected from the group consisting of silver salts, iodophors, iodine, benzoic acid, dihydroacetic acid, propionic acid, sorbic acid, methyl paraben, ethyl paraben, propyl paraben, butyl paraben, cetrimide, benzalkonium chloride, dequalinium chloride, chlorhexidine, chloroeresol, chlorxylenol, benzyl alcohol, bronopol, chlorbutanol, phenoxyethanol, phenylethyl alcohol, 2,4-dichlorobenzyl alcohol, thiomersal, clindamycin, erythromycin, benzoyl peroxide, mupirocin, bacitracin, polymyxin B, neomycin, triclosan, parachlorometaxylene, foscarnet, miconazole, fluconazole, itriconazole, ketoconazole, silver sulfadiazine, octoxyglycerine, biguanides such as, but not limited to, chlorhexidine free base, chlorhexidine palmitate, chlorhexidine diphosphanilate, chlorhexidine digluconate, chlorhexidine diacetate, chlorhexidine dihydrochloride, chlorhexidine dichloride, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidine dipropionate, chlorhexidine di-iodobutyrate, chlorhexidine di-n-valerate, chlorhexidine dicaproate, chlorhexidine malonate, chlorhexidine succinate, chlorhexidine malate, chlorhexidine tartrate, chlorhexidine dimonoglycolate, chlorhexidine monodiglycolate, chlorhexidine dilactate, chlorhexidine di-α-hydroxyisobutyrate, chlorhexidine diglucoheptonate, chlorhexidine di-isothionate, chlorhexidine dibenzoate, chlorhexidine dicinnamate, chlorhexidine dimandelate, chlorhexidine di-isophthalate, chlorhexidine di-2-hydroxynapthoate, chlorhexidine embonate, and para-hexamethylenebiguanide ("PHMB").

In various non-limiting embodiments, a personal care product may comprise a neutralizing agent to neutralize carboxyl groups present in one or more other component, such as carboxyl groups in a thickening agent. Suitable neutralizing agents include diisopropylamine and triethanolamine.

In various non-limiting embodiments, the composition may comprise a surfactant. The surfactant may be an anionic surfactant, a cationic surfactant, an ampholytic surfactant, or a nonionic surfactant. Examples of nonionic surfactants include polyethoxylates, fatty alcohols (e.g., ceteth-20 (a cetyl ether of polyethylene oxide having an average of about 20 ethylene oxide units) and other "BRIJ®" nonionic surfactants available from ICI Americas, Inc. (Wilmington, Del.)), cocamidopropyl betaine, alkyl phenols, fatty acid esters of sorbitol, sorbitan, or polyoxyethylene sorbitan. A specific non-limiting example of a non-ionic surfactant is Glucopon® 215 (Cognis), an aqueous solution of alkyl polyglycosides based on a natural fatty alcohol C8-C10. Suitable anionic surfactants include ammonium lauryl sulfate and lauryl ether sulfosuccinate.

In various non-limiting embodiments, a personal care product may comprise water.

In various non-limiting embodiments, a compositions used in a personal care product may comprise a hydrogel comprising, for example, a compound such as hydroxypropylmethyl cellulose, cationic hydroxyethyl cellulose (U-care polymers), ethyl cellulose, hydroxypropyl cellulose, hydroxymethyl cellulose, carboxy methyl cellulose, polyethylene oxide (polyox resins), and chitosan pyrrolidone carboxylate (Kytomer PC).

In various non-limiting embodiments, a personal care product may comprise an alcohol or a mixture of alcohols, for example, ethanol, isopropyl alcohol, n-propyl alcohol, and mixtures thereof; fatty alcohols, including, but not limited to, cetyl alcohol, myristol alcohol, stearyl alcohol, octyl alcohol, decyl alcohol and lauryl alcohol, and mixtures thereof; and hexanol.

In various non-limiting embodiments, the compositions used in a personal care product may comprise a silicone polymer, for example one or more than one polydimethylsiloxane polymer (Dow Corning 225 Silicone Fluid), dimethiconol fluid in dimethicone (Dow Corning 1403 Silicone Fluid), cyclomethicone and dimethicone copolyl (Dow Corning 3225C Silicone Fluid), and silicone glycol (BASF 1066 DCG polyol).

In various non-limiting embodiments, a compositions used in a personal care product may comprise an emollient solvent such as a glycidyl ether having an alkyl chain up to and including 18 carbon molecules and ethoxylates and propoxylates thereof, a glyceryl ether having an alkyl chain up to and including 18 carbon molecules and ethoxylates and propoxylates thereof, a mono- or diglyceryl ether having an alkyl chain up to and including 18 carbon molecules and ethoxylates and propoxylates thereof, ethoxylate and propoxylate ethers, ethoxy diglycol esters, ethyl hexyl alcohol propoxylate, and propylene glycol esther ethoxylates and propoxylates, and Arlarnol (Altas).

In various non-limiting embodiments, a composition used in a personal care product may comprise one or more additive such as a dye, fragrance, pH adjuster, including basic pH adjusters such as ammonia, mono-, di- and tri-alkyl amines, mono-, di- and tri-alkanolamines, alkali metal and alkaline earth metal hydroxides (e.g., ammonia, sodium hydroxide, potassium hydroxide, lithium hydroxide, monoethanolamine, triethylamine, isopropylamine, diethanolamine and triethanolamine); acid pH adjusters such as mineral acids and polycarboxylic acids (e.g., hydrochloric acid, nitric acid, phosphoric acid, sulfuric acid, citric acid, glycolic acid, and lactic acid); a vitamin such as vitamin A, vitamin E and vitamin C; a polyamino acid or salt thereof, ethylenediamine tetraacidic acid (EDTA), a preservative such as Germall plus or DMDM hydantoin, and/or a sunscreen such as aminobenzoic acid, arobenzone, cinoxate, diioxybenzone, homosalate, menthyl anthranilate, octocrylene, octyl methoxycinnamate, octyl salicylate, oxybenzoate, padimate O, phenylbenzimidazole, sulfonic acid, sulisobenzone, titanium dioxide, trolamine salicylate and zinc oxide.

In one set of non-limiting embodiments, a personal care composition has both antimicrobial and anti-inflammatory (AM-AI) activities, and, for example, may be used as a skin cleanser or topical cream.

The present subject matter also provides for rapidly acting AMI hand disinfectant lotions. The combination of GSE, Benzyl alcohol and 1,3 propanediol when used along with the anti inflammatory agent CRMN, edible plant extract (Kefiprotect®) and Pomegranate seed oil (PSO) exhibits additional antimicrobial activity.

The present subject matter also contemplates rapidly acting botanical AM-AI hand disinfectant lotions.

In specific, non-limiting embodiments, the present subject matter provides for the preparation of topical cream formulations containing anti-irritant, anti-inflammatory agents, gelling agents, and botanicals for minor cuts and wounds.

Antifungal activity of antifungal agents can be significantly enhanced by the use of a combination of alcohols such as benzyl alcohol, fruit acids, and optionally biguanide and benzalkonium chloride.

The present subject matter also provides formulations containing GSE, benzyl alcohol, Zemea®, THC, and a coconut based phospholipid for alcohol-based hand sanitizer (AHS) compositions.

The present subject matter also provides for alcohol free botanical hand disinfectant lotions comprising between about 0.5% and 2% (w/w) benzyl alcohol; between about 0.3% and 2% (w/w) silicone fluid; between about 0.1% and 0.5% (w/w) zinc oxide; between about 0.1% and 2% (w/w) fruit acid, for example, lactic acid or citric acid; between about 0.05% and 1% (w/w) of one or more botanical selected from aloe gel, GSE, citrus extract, wasabi extract, willow bark extract, aspen bark extract and honeysuckle extract; and between about 0.1% and 0.5% (w/w) of one or more essential oil selected from oregano oil, pomegranate oil, rosemary oil, lemongrass oil and cinnamon oil (e.g., cinnamon leaf oil or cinnamon bark oil). Such compositions can optionally comprise between about 0.5% and 2% (w/w) farnesol, between about 0.05% and 0.3% (w/w) thymol, and/or between about 0.2% and 1% alkanediol.

Non-limiting examples of alcohol free botanical hand disinfectant lotion formulations are as follows.

| Alcohol Free Botanical Hand Disinfectant Lotion A | |
|---|---|
| Ingredients | Range (% w/w) |
| Water | 60-94.6 |
| Hydroxypropyl methyl-cellulose stearoxy ether (Sangelose) | 0.05-0.3 |
| Allantoin | 0.1-0.3 |
| Polowax NF | 0.5-2.0 |
| Incroquat TMS | 0.5-4.0 |
| Stearyl alcohol | 0.5-3.0 |
| Vit. E acetate | 0.02-0.2 |
| Vit. C | 0.02-0.2 |
| Zinc oxide | 0.1-0.5 |
| Glycerin | 1.0-3.0 |
| Butylene glycol | 0.5-3.0 |
| Benzyl alcohol | 0.5-2.0 |
| Silicone fluid | 0.3-2.0 |
| Lactic acid | 0.1-2.0 |
| Aloe gel | 0.01-2.0 |
| Symrelief | 0.01-1.0 |
| Pentanediol | 0-1.0 |
| Pomegranate oil | 0-1.0 |
| Oregano oil | 0.1-0.3 |
| Thymol | 0.05-0.3 |
| Rosemary oil | 0.1-1.0 |
| Lemongrass oil | 0.1-0.5 |
| Grapefruit seed/other Citrus extract | 0.3-1.0 |
| Wasabi extract | 0.1-0.5 |
| Benzoic acid | 0.2-0.5 |
| Sodium Benzoate | 0.2-0.5 |
| Adjust pH to 5.5-6.0 | |

A specific non-limiting specific example of an alcohol free botanical hand disinfectant lotion formulation of the present application includes the following formulation.

| Alcohol Free Botanical Hand Disinfectant Lotion A | |
|---|---|
| Ingredients | % w/w |
| Water | 89.25 |
| Hydroxypropyl methyl-cellulose stearoxy ether (Sangelose) | 0.2 |
| Allantoin | 0.3 |
| Polowax NF | 0.5 |
| Incroquat TMS | 0.5 |
| Stearyl alcohol | 0.5 |
| Vit. E acetate | 0.1 |
| Vit. C | 0.1 |
| Zinc oxide | 0.3 |
| Glycerin | 2.0 |
| Butylene glycol | 1.0 |
| Benzyl alcohol | 1.0 |
| Silicone fluid | 1.0 |
| Lactic acid | 0.2 |
| Aloe gel | 1.0 |
| Symrelief | 0.05 |
| Pomegranate oil | 0.3 |
| Oregano oil | 0.1 |
| Thymol | 0.1 |
| Rosemary oil | 0.1 |
| Lemongrass oil | 0.2 |
| Grapefruit seed/other Citrus extract | 0.5 |
| Wasabi extract | 0.3 |
| Benzoic acid | 0.2 |
| Sodium Benzoate | 0.2 |
| Adjust pH to 5.5-6.0 | |

A non-limiting general example of an alcohol free botanical hand disinfectant lotion formulation of the present application includes the following formulation.

| Alcohol Free Botanical Hand Disinfectant Lotion B | |
|---|---|
| Ingredients | Range (% w/w) |
| Water | 60-94.6 |
| Hydroxypropyl methyl-cellulose stearoxy ether (Sangelose) | 0.05-0.3 |
| Allantoin | 0.1-0.3 |
| Polowax NF | 0.5-2.0 |
| Incroquat TMS | 0.5-4.0 |
| Stearyl alcohol | 0.5-3.0 |
| Vit. E acetate | 0.02-0.2 |
| Vit. C | 0.02-0.2 |
| Zinc oxide | 0.1-0.5 |
| Glycerin | 1.0-3.0 |
| Butylene glycol | 0.5-3.0 |
| Benzyl alcohol | 0.5-2.0 |
| Silicone fluid | 0.3-2.0 |
| Lactic acid | 0.1-2.0 |
| Aloe gel | 0.01-2.0 |
| Symrelief | 0.01-1.0 |
| Pentanediol | 0.2-1.0 |
| Pomegranate oil | 0-1.0 |
| Rosemary oil | 0.05-1.0 |
| Lemongrass oil | 0.05-0.5 |
| Cinnamon oil | 0.05-0.2 |
| Farnesol//Bisabolol | 0.3-2.0 |
| Thymol | 0.05-0.3 |
| Willow Bark extract | 0-2.0 |
| Aspen Bark extract | 0-2.0 |
| Wasabi extract | 0.1-0.5 |
| Benzoic acid | 0.2-0.5 |
| Sodium Benzoate | 0.2-0.5 |
| Adjust pH to 5.5-6.0 | |

A specific non-limiting specific example of an alcohol free botanical hand disinfectant lotion formulation of the present application includes the following formulation.

| Alcohol Free Botanical Hand Disinfectant Lotion B | |
|---|---|
| Ingredients | % w/w |
| Water | 86.90 |
| Hydroxypropyl methyl-cellulose stearoxy ether (Sangelose) | 0.2 |
| Allantoin | 0.3 |
| Polowax NF | 0.5 |
| Incroquat TMS | 0.5 |
| Stearyl alcohol | 0.5 |
| Vit. E acetate | 0.1 |
| Vit. C | 0.1 |
| Zinc oxide | 0.3 |
| Glycerin | 2.0 |
| Butylene glycol | 1.0 |
| Benzyl alcohol | 1.0 |
| Silicone fluid | 1.0 |
| Lactic acid | 0.2 |
| *Aloe* gel | 1.0 |
| Symrelief | 0.05 |
| Pentanediol | 1.0 |
| Pomegranate oil | 0.3 |
| Rosemary oil | 0.05 |
| Lemongrass oil | 0.1 |
| Cinnamon oil | 0.1 |
| Farnesol//Bisabolol | 0.5 |
| Thymol | 0.1 |
| Willow Bark extract | 1.0 |
| Aspen Bark extract | 0.5 |
| Wasabi extract | 0.3 |
| Benzoic acid | 0.2 |
| Sodium Benzoate | 0.2 |
| Adjust pH to 5.5-6.0 | |

A non-limiting general example of an alcohol free botanical hand disinfectant lotion formulation of the present application includes the following formulation.

| Alcohol Free Botanical Hand Disinfectant Lotion | |
|---|---|
| Ingredients | Range (% w/w) |
| Water | 60-93.9 |
| Soft cat polymer | 0.1-0.5 |
| Allantoin | 0.1-0.3 |
| Polowax NF | 0.5-2.0 |
| Incroquat TMS | 0.5-4.0 |
| Stearyl alcohol | 0.5-3.0 |
| Isopropyl myristate | 0.5-2.0 |
| Arlacel 165 | 0.5-1.0 |
| Vit. E acetate | 0.02-0.5 |
| Zinc oxide | 0.1-0.5 |
| Glycerin | 1.0-3.0 |
| Butylene glycol | 0.5-3.0 |
| Lactic acid | 0.1-2.0 |
| Benzyl alcohol | 0.5-2.0 |
| Silicone fluid | 0.3-1.0 |
| Lactic acid | 0.1-2.0 |
| *Aloe* gel | 0.01-2.0 |
| Symrelief | 0.01-1.0 |
| Pentanediol | 0-1.0 |
| Pomegranate oil | 0-1.0 |
| Rosemary oil | 0.1-1.0 |
| Lemongrass oil | 0.1-0.5 |
| Honeysuckle extract | 0.1-0.5 |
| Wasabi extract | 0.1-0.5 |
| Benzoic acid | 0.2-0.5 |
| Sodium Benzoate | 0.2-0.5 |
| Adjust pH to 5.5-6.0 | |

A specific non-limiting specific example of an alcohol free botanical hand disinfectant lotion formulation of the present application includes the following formulation.

| Alcohol Free Botanical Hand Disinfectant Lotion | |
|---|---|
| Ingredients | % ww |
| Water | 82.35 |
| Soft cat polymer | 0.3 |
| Allantoin | 0.3 |
| Polowax NF | 2.0 |
| Incroquat TMS | 2.0 |
| Stearyl alcohol | 2.0 |
| Isopropyl myristate | 1.0 |
| Arlacel 165 | 1.0 |
| Vit. E acetate | 0.1 |
| Zinc oxide | 0.3 |
| Glycerin | 2.0 |
| Butylene glycol | 1.0 |
| Lactic acid | 0.2 |
| Benzyl alcohol | 1.0 |
| Silicone fluid | 1.0 |
| Lactic acid | 0.2 |
| *Aloe* gel | 0.5 |
| Symrelief | 0.05 |
| Pentanediol | 1.0 |
| Pomegranate oil | 0.3 |
| Rosemary oil | 0.2 |
| Lemongrass oil | 0.2 |
| Honeysuckle extract | 0.3 |
| Wasabi extract | 0.3 |
| Benzoic acid | 0.2 |
| Sodium Benzoate | 0.2 |
| Adjust pH to 5.5-6.0 | |

The present subject matter also provides for aqueous botanical hand disinfectant lotions containing benzyl alcohol and botanicals. A non-limiting general example of such a formulation includes the following.

| Aqueous Botanical Hand Disinfectant Lotion A | |
|---|---|
| Ingredients | Range (% w/w) |
| Water | 49.7-85.1 |
| Hydroxypropyl methyl-cellulose stearoxy ether (Sangelose) | 0.05-0.2 |
| Allantoin | 0.1-0.3 |
| Polowax NF | 0.5-2.0 |
| Incroquat TMS | 0.5-4.0 |
| Stearyl alcohol | 0.5-3.0 |
| Vit. E acetate | 0.02-0.5 |
| Glycerin | 1.0-3.0 |
| Zinc oxide | 0.1-0.5 |
| Butylene glycol | 0.5-3.0 |
| Lactic acid | 0.1-2.0 |
| Benzyl alcohol | 0.5-2.0 |
| Silicone fluid | 0.3-2.0 |
| *Aloe* gel | 0.01-2.0 |
| Plant based alcohol (SDA40B from corn) | 10-20 |
| Pomegranate oil | 0-1.0 |
| Rosemary oil | 0.1-1.0 |
| Lemongrass oil | 0.1-0.5 |
| Thymol | 0.05-0.3 |
| Honeysuckle extract | 0.1-1.0 |
| Grapefruit seed/other *citrus* extract | 0-0.5 |
| Wasabi extract | 0.0-0.5 |
| Benzoic acid | 0.2-0.5 |
| Sodium Benzoate | 0.2-0.5 |
| Adjust pH to 5.5-6.0 | |

A specific non-limiting specific example of an aqueous botanical hand disinfectant lotion containing benzyl alcohol and botanicals of the present application includes the following formulation.

| Aqueous Botanical Hand Disinfectant Lotion A | |
|---|---|
| Ingredients | % w/w |
| Water | 79.1 |
| Hydroxypropyl methyl-cellulose stearoxy ether (Sangelose) | 0.1 |
| Allantoin | 0.3 |
| Polowax NF | 0.5 |
| Incroquat TMS | 0.5 |
| Stearyl alcohol | 0.5 |
| Vit. E acetate | 0.1 |
| Glycerin | 1.0 |
| Zinc oxide | 0.3 |
| Butylene glycol | 1.0 |
| Lactic acid | 0.2 |
| Benzyl alcohol | 1.0 |
| Silicone fluid | 1.0 |
| *Aloe* gel | 2.0 |
| Plant based alcohol (SDA40B from corn) | 10 |
| Pomegranate oil | 0.3 |
| Rosemary oil | 0.3 |
| Lemongrass oil | 0.2 |
| Thymol | 0.1 |
| Honeysuckle extract | 0.3 |
| Grapefruit seed/other *citrus* extract | 0.5 |
| Wasabi extract | 0.3 |
| Benzoic acid | 0.2 |
| Sodium Benzoate | 0.2 |
| Adjust pH to 5.5-6.0 | |

A non-limiting general example of an aqueous botanical hand disinfectant lotion containing benzyl alcohol and botanicals of the present application includes the following formulation.

| Aqueous Botanical Hand Disinfectant Lotion B | |
|---|---|
| Ingredients | Range (% w/w) |
| Water | 49.5-84.97 |
| Hydroxypropyl methyl-cellulose stearoxy ether (Sangelose) | 0.05-0.2 |
| Allantoin | 0.1-0.3 |
| Polowax NF | 0.5-2.0 |
| Incroquat TMS | 0.5-4.0 |
| Stearyl alcohol | 0.5-3.0 |
| Vit. E acetate | 0.02-0.5 |
| Zinc oxide | 0.1-0.3 |
| Glycerin | 1.0-5.0 |
| Benzyl alcohol | 0.5-2.0 |
| Silicone fluid | 0.3-1.0 |
| Aloe gel | 0.01-2.0 |
| Plant based alcohol (SDA40B from corn) | 10-20 |
| Pomegranate oil | 0-1.0 |
| Rosemary oil | 0-1.0 |
| Lemongrass oil | 0.1-0.5 |
| Thymol | 0.05-0.2 |
| Wasabi extract | 0.3-0.5 |
| Willow Bark extract | 0.-2.0 |
| Aspen Bark extract | 0.-2.0 |
| Farnesol/Bisabolol | 0.3-1.0 |
| Cationic surfactant | 0.3-1.0 |
| Benzoic acid | 0.2-0.5 |
| Sodium Benzoate | 0.2-0.5 |
| Adjust pH to 5.5-6.0 | |

A non-limiting specific example of an aqueous botanical hand disinfectant lotion containing benzyl alcohol and botanicals of the present application includes the following formulation.

| Aqueous Botanical Hand Disinfectant Lotion B | |
|---|---|
| Ingredients | % w/w |
| Water | 73.5 |
| Hydroxypropyl methyl-cellulose stearoxy ether (Sangelose) | 0.1 |
| Allantoin | 0.2 |
| Polowax NF | 0.5 |
| Incroquat TMS | 0.5 |
| Stearyl alcohol | 0.5 |
| Vit. E acetate | 0.1 |
| Zinc oxide | 0.3 |
| Glycerin | 1.0 |
| Benzyl alcohol | 1.0 |
| Silicone fluid | 2.0 |
| Aloe gel | 2.0 |
| Plant based alcohol (SDA40B from corn) | 15 |
| Pomegranate oil | 0.3 |
| Rosemary oil | 0.1 |
| Lemongrass oil | 0.1 |
| Thymol | 0.1 |
| Wasabi extract | 0.3 |
| Willow Bark extract | 0.5 |
| Aspen Bark extract | 0.5 |
| Farnesol/Bisabolol | 0.5 |
| Cationic surfactant | 0.5 |
| Benzoic acid | 0.2 |
| Sodium Benzoate | 0.2 |
| Adjust pH to 5.5-6.0 | |

A non-limiting general example of an aqueous botanical hand disinfectant lotion containing benzyl alcohol and botanicals of the present application includes the following formulation.

| Aqueous Botanical Hand Disinfectant Lotion 1 | |
|---|---|
| Ingredients | Range (% w/w) |
| Water | 49.2-84.1 |
| Allantoin | 0.1-0.3 |
| Polowax NF | 0.5-2.0 |
| Incroquat TMS | 0.5-4.0 |
| Stearyl alcohol | 0.5-3.0 |
| Isopropyl myristate | 0.5-2.0 |
| Arlacel 165 | 0.5-1.0 |
| Vit. E acetate | 0.02-0.5 |
| Zinc oxide | 0.1-0.5 |
| Glycerin | 1.0-3.0 |
| Butylene glycol | 0.5-3.0 |
| Lactic acid | 0.1-2.0 |
| Benzyl alcohol | 0.5-2.0 |
| Silicone fluid | 0.3-1.0 |
| Aloe gel | 0.01-2.0 |
| Plant based alcohol (SDA40B from corn) | 10-20 |
| Pomegranate oil | 0-1.0 |
| Rosemary oil | 0.3-1.0 |
| Lemongrass oil | 0.1-0.5 |
| Grapefruit seed extract | 0-0.5 |
| Wasabi extract | 0-0.5 |
| Benzoic acid | 0.2-0.5 |
| Sodium Benzoate | 0.2-0.5 |
| Adjust pH to 5.5-6.0 | |

A non-limiting specific example of an aqueous botanical hand disinfectant lotion containing benzyl alcohol and botanicals of the present application includes the following formulation.

| Aqueous Botanical Hand Disinfectant Lotion 1 | |
|---|---|
| Ingredients | % w/w |
| Water | 72.3 |
| Allantoin | 0.3 |
| Polowax NF | 2.0 |
| Incroquat TMS | 2.0 |
| Stearyl alcohol | 2.0 |
| Isopropyl myristate | 1.0 |
| Arlacel 165 | 1.0 |
| Vit. E acetate | 0.1 |
| Zinc oxide | 0.3 |
| Glycerin | 2.0 |
| Butylene glycol | 1.0 |
| Lactic acid | 0.2 |
| Benzyl alcohol | 1.0 |
| Silicone fluid | 1.0 |
| Aloe gel | 2.0 |
| Plant based alcohol (SDA40B from corn) | 10 |
| Pomegranate oil | 0.3 |
| Rosemary oil | 0.3 |
| Lemongrass oil | 0.2 |
| Grapefruit seed extract | 0.3 |
| Wasabi extract | 0.3 |
| Benzoic acid | 0.2 |
| Sodium Benzoate | 0.2 |
| Adjust pH to 5.5-6.0 | |

A non-limiting general example of an aqueous botanical hand disinfectant lotion containing benzyl alcohol and botanicals of the present application includes the following formulation.

| Aqueous Botanical Hand Disinfectant Lotion 2 | |
|---|---|
| Ingredients | Range (% w/w) |
| Water | 52.3-85.3 |
| Hydroxypropyl methyl-cellulose stearoxy ether (Sangelose) | 0.05-0.2 |
| Allantoin | 0.1-0.3 |
| Polowax NF | 0.5-2.0 |
| Incroquat TMS | 0.5-4.0 |
| Stearyl alcohol | 0.5-3.0 |
| Vit. E acetate | 0.02-0.5 |
| Zinc oxide | 0.1-0.5 |
| Glycerin | 1.0-5.0 |
| Benzyl alcohol | 0.5-2.0 |
| Silicone fluid | 0.3-1.0 |
| Aloe gel | 0.01-2.0 |
| Plant based alcohol (SDA40B from corn) | 10-20 |
| Pomegranate oil | 0-1.0 |
| Rosemary oil | 0-1.0 |
| Lemongrass oil | 0.1-0.5 |
| Thymol | 0.05-0.2 |
| Galangal oil | 0.02-0.5 |
| Grapefruit seed extract | 0-0.5 |
| Wasabi extract | 0-0.5 |
| Farnesol/Bisabolol | 0.3-1.0 |
| Cetrimonium chloride | 0.3-1.0 |
| Benzoic acid | 0.2-0.5 |
| Sodium Benzoate | 0.2-0.5 |
| Adjust pH to 5.5-6.0 | |

A non-limiting specific example of an aqueous botanical hand disinfectant lotion containing benzyl alcohol and botanicals of the present application includes the following formulation.

| Aqueous Botanical Hand Disinfectant Lotion 2 | |
|---|---|
| Ingredients | % w/w |
| Water | 73.15 |
| Hydroxypropyl methyl-cellulose stearoxy ether (Sangelose) | 0.1 |
| Allantoin | 0.2 |
| Polowax NF | 0.5 |
| Ineroquat TMS | 0.5 |
| Stearyl alcohol | 0.5 |
| Vit. E acetate | 0.1 |
| Zinc oxide | 0.1 |
| Glycerin | 2.0 |
| Benzyl alcohol | 1.0 |
| Silicone fluid | 2.0 |
| Aloe gel | 2.0 |
| Plant based alcohol (SDA40B from corn) | 15 |
| Pomegranate oil | 0.3 |
| Rosemary oil | 0.3 |
| Lemongrass oil | 0.2 |
| Thymol | 0.1 |
| Galangal oil | 0.05 |
| Grapefruit seed extract | 0.5 |
| Farnesol/Bisabolol | 0.5 |
| Cetrimonium chloride | 0.5 |
| Benzoic acid | 0.2 |
| Sodium Benzoate | 0.2 |
| Adjust pH to 5.5-6.0 | |

A non-limiting general example of an aqueous botanical hand disinfectant lotion containing benzyl alcohol and botanicals of the present application includes the following formulation.

| Aqueous Botanical Hand Disinfectant Lotion 3 | |
|---|---|
| Ingredients | Range (% w/w) |
| Water | 52.3-85.3 |
| Hydroxypropyl methyl-cellulose stearoxy ether (Sangelose) | 0.05-0.2 |
| Hydroxypropyl methyl cellulose | 0.05-0.2 |
| Allantoin | 0.1-0.4 |
| Propylene glycol | 0.5-2.0 |
| Polowax NF | 0.5-2.0 |
| Incroquat TMS | 0.5-4.0 |
| Stearyl alcohol | 0.5-3.0 |
| Vit. E acetate | 0.02-0.5 |
| Zinc oxide | 0.1-0.5 |
| Glycerin | 1.0-5.0 |
| Benzyl alcohol | 0.5-2.0 |
| Silicone fluid | 0.3-1.0 |
| Aloe gel | 0.01-2.0 |
| Plant based alcohol (SDA40B from corn) | 10-20 |
| Pomegranate oil | 0-1.0 |
| Lemongrass oil | 0.1-0.5 |
| Thymol | 0.05-0.2 |
| Cinnamon oil | 0.05-1.0 |
| Bisabolol | 0.01-1.0 |
| Cetrimonium chloride | 0.3-1.0 |
| Adjust pH to 5.5-6.0 | |

A non-limiting specific example of an aqueous botanical hand disinfectant lotion containing benzyl alcohol and botanicals of the present application includes the following formulation.

| Aqueous Botanical Hand Disinfectant Lotion 3 | |
|---|---|
| Ingredients | % w/w |
| Water | 73.95 |
| Hydroxypropyl methyl-cellulose stearoxy ether (Sangelose) | 0.1 |

Aqueous Botanical Hand Disinfectant Lotion 3

| Ingredients | % w/w |
| --- | --- |
| Hydroxypropyl methyl cellulose | 0.2 |
| Allantoin | 0.3 |
| Propylene glycol | 1.0 |
| Polowax NF | 0.5 |
| Incroquat TMS | 1.5 |
| Stearyl alcohol | 0.5 |
| Vit. E acetate | 0.1 |
| Zinc oxide | 0.3 |
| Glycerin | 2.0 |
| Benzyl alcohol | 1.0 |
| Silicone fluid | 2.0 |
| Aloe gel | 0.5 |
| Plant based alcohol (SDA40B from corn) | 15 |
| Pomegranate oil | 0.2 |
| Lemongrass oil | 0.1 |
| Thymol | 0.1 |
| Cinnamon leaf oil | 0.1 |
| Bisabolol | 0.05 |
| Cetrimonium chloride | 0.5 |
| Adjust pH to 5.5-6.0 | |

The present subject matter also provides for aqueous botanical hand disinfectant foams containing benzyl alcohol and botanicals. A non-limiting general example of such a formulation includes the following.

Aqueous Botanical Hand Disinfectant Foam A

| Ingredients | Range (% w/w) |
| --- | --- |
| Water | 52.7-89.9 |
| Hydroxypropyl methyl-cellulose stearoxy ether (Sangelose) | 0.05-0.2 |
| Allantoin | 0.2-0.5 |
| Grapefruit seed extract | 0.3-1.0 |
| Solubulizer (Peg-40 hydrogenated Castor oil, Trideceth 9, water) | 1-3 |
| SDA-40 B (natural) | 5.0-20 |
| Benzyl alcohol | 0.1-2.0 |
| Pentylene glycol | 0.5-3.0 |
| Phenoxyethanol | 0.5-1.0 |
| Aloe leaf juice | 0.05-2.0 |
| Bisabolol | 0.025-0.1 |
| Wasabi extract | 0.2-0.5 |
| Honeysuckle extract | 0.2-0.5 |
| Linalool | 0.05-0.3 |
| Lemongrass oil | 0.02-2.0 |
| Thymol | 0.05-0.2 |
| Phospholipid PTM (Croda) | 0-1.0 |
| Farnesol/Bisabolol | 0.3-1.0 |
| Cationic surfactant | 0.5-2.0 |
| Benzoic acid | 0.02-2.0 |
| Glucopon | 0.5-3.0 |
| Silicone (silsurf) | 0.5-2.0 |
| Adjust pH = 4.0-4.5 | |

A non-limiting specific example of an aqueous botanical hand disinfectant foam containing benzyl alcohol and botanicals of the present application includes the following formulation.

Aqueous Botanical Hand Disinfectant Foam A

| Ingredients | % w/w |
| --- | --- |
| Water | 78.15 |
| Hydroxypropyl methyl-cellulose stearoxy ether (Sangelose) | 0.1 |
| Allantoin | 0.3 |
| Grapefruit seed extract | 0.5 |

Aqueous Botanical Hand Disinfectant Foam A

| Ingredients | % w/w |
| --- | --- |
| Solubulizer (Peg-40 hydrogenated Castor oil, Trideceth 9, water) | 2.0 |
| SDA-40 B (natural) | 10 |
| Benzyl alcohol | 1.0 |
| Pentylene glycol | 1.0 |
| Phenoxyethanol | 1.0 |
| Aloe leaf juice | 0.5 |
| Bisabolol | 0.05 |
| Wasabi extract | 0.3 |
| Honeysuckle extract | 0.3 |
| Linalool | 0.1 |
| Lemongrass oil | 0.2 |
| Thymol | 0.1 |
| Phospholipid PTM (Croda) | 0.5 |
| Farnesol/Bisabolol | 0.5 |
| Cationic surfactant | 0.5 |
| Benzoic acid | 0.2 |
| Glucopon | 1.3 |
| Silicone (silsurf) | 1.4 |
| Adjust pH = 4.0-4.5 | |

A non-limiting general example of an aqueous botanical hand disinfectant foam containing benzyl alcohol and botanicals of the present application includes the following formulation.

Aqueous Botanical Hand Disinfectant Foam B

| Ingredients | Range (% w/w) |
| --- | --- |
| Water | 54.7-90.8 |
| Hydroxypropyl methyl-cellulose stearoxy ether (Sangelose) | 0.05-0.2 |
| Allantoin | 0.2-0.5 |
| Solubulizer (Peg-40 hydrogenated Castor oil, Trideceth 9, water) | 1-3 |
| SDA-40 B (natural) | 5.0-20 |
| Benzyl alcohol | 0.1-2.0 |
| Pentylene glycol | 0.5-3.0 |
| Phenoxyethanol | 0.5-1.0 |
| Aloe leaf juice | 0.05-2.0 |
| Bisabolol | 0.025-0.1 |
| Linalool | 0.05-0.3 |
| Lemongrass oil | 0.02-2.0 |
| Farnesol | 0.3-2.0 |
| Thymol | 0.05-0.2 |
| Phospholipid PTM (Croda) | 0-1.0 |
| Benzoic acid | 0.02-2.0 |
| Cationic surfactant | 0.3-1.0 |
| Glucopon | 0.5-3.0 |
| Silicone (silsurf) | 0.5-2.0 |
| Adjust pH = 4.0-4.5 | |

A non-limiting specific example of an aqueous botanical hand disinfectant foam containing benzyl alcohol and botanicals of the present application includes the following formulation.

Aqueous Botanical Hand Disinfectant Foam B

| Ingredients | % w/w |
| --- | --- |
| Water | 80.65 |
| Hydroxypropyl methyl-cellulose stearoxy ether (Sangelose) | 0.1 |
| Allantoin | 0.3 |
| Solubulizer (Peg-40 hydrogenated Castor oil, Trideceth 9, water) | 2.0 |
| SDA-40 B (natural) | 10 |
| Benzyl alcohol | 1.0 |
| Pentylene glycol | 1.0 |
| Phenoxyethanol | 1.0 |

| Aqueous Botanical Hand Disinfectant Foam B | |
|---|---|
| Ingredients | % w/w |
| Aloe leaf juice | 0.5 |
| Bisabolol | 0.05 |
| Linalool | 0.1 |
| Lemongrass oil | 0.1 |
| Farnesol | 0.5 |
| Thymol | 0.1 |
| Benzoic acid | 0.2 |
| Cationic surfactant | 0.5 |
| Glucopon | 0.5 |
| Silicone (silsurf) 1.4 | |
| Adjust pH = 4.0-4.5 | |

A non-limiting general example of an aqueous botanical hand disinfectant foam containing benzyl alcohol and botanicals of the present application includes the following formulation.

| Aqueous Botanical Hand Disinfectant Foam 1 | |
|---|---|
| Ingredients | Range (% w/w) |
| Water | 58-91.5 |
| Kytamer (Chitosan complex) | 0.05-0.4 |
| Allantoin | 0.2-0.5 |
| Cetrimonium chloride | 0.1-1.0 |
| Honeysuckle extract | 0.3-1.0 |
| Solubulizer (Peg-40 hydrogenated Castor oil, Trideceth 9, water) | 1-3 |
| SDA-40 B (natural) | 5.0-20 |
| Benzyl alcohol | 0.1-2.0 |
| Phenoxyethanol | 0.5-1.0 |
| Aloe leaf juice | 0.05-2.0 |
| Bisabolol | 0.025-0.1 |
| Linalool | 0.05-0.3 |
| Lemongrass oil | 0.02-2.0 |
| Thymol | 0.05-0.2 |
| Galangal oil | 0.02-0.5 |
| Phospholipid PTM (Croda) | 0-1.0 |
| Benzoic acid | 0.02-2.0 |
| Glucopon | 0.5-3.0 |
| Silicone (silsurf) | 0.5-2.0 |
| Adjust pH = 4.0-4.5 or to pH = 5.5-6.0 | |

A non-limiting specific example of an aqueous botanical hand disinfectant foam containing benzyl alcohol and botanicals of the present application includes the following formulation.

| Aqueous Botanical Hand Disinfectant Foam 1 | |
|---|---|
| Ingredients | % w/w |
| Water | 81.65 |
| Kytamer (Chitosan complex) | 0.2 |
| Allantoin | 0.3 |
| Cetrimonium chloride | 0.5 |
| Honeysuckle extract | 0.5 |
| Solubulizer (Peg-40 hydrogenated Castor oil, Trideceth 9, water) | 2.0 |
| SDA-40 B (natural) | 10 |
| Benzyl alcohol | 1.0 |
| Phenoxyethanol | 1.0 |
| Aloe leaf juice | 0.5 |
| Bisabolol | 0.05 |
| Linalool | 0.1 |
| Lemongrass oil | 0.2 |
| Thymol | 0.1 |
| Galangal oil | 0.05 |
| Benzoic acid | 0.1 |
| Glucopon | 0.75 |
| Silicone (silsurf) | 1.0 |
| Adjust pH = 4.0-4.5 or to pH = 5.5-6.0 | |

A non-limiting general example of an aqueous botanical hand disinfectant foam containing benzyl alcohol and botanicals of the present application includes the following formulation.

| Aqueous Botanical Hand Disinfectant Foam A1 | |
|---|---|
| Ingredients | Range (% w/w) |
| Water | 53.7-90.3 |
| Hydroxypropyl methyl-cellulose stearoxy ether (Sangelose) | 0.05-0.2 |
| Allantoin | 0.2-0.5 |
| Grapefruit seed extract | 0.3-1.0 |
| Solubulizer (Peg-40 hydrogenated Castor oil, Trideceth 9, water) | 1-3 |
| SDA-40 B (natural) | 5.0-20 |
| Benzyl alcohol | 0.1-2.0 |
| Pentylene glycol | 0.5-3.0 |
| Phenoxyethanol | 0.5-1.0 |
| Aloe leaf juice | 0.05-2.0 |
| Bisabolol | 0.025-0.1 |
| Linalool | 0.05-0.3 |
| Lemongrass oil | 0.02-2.0 |
| Thymol | 0.05-0.2 |
| Phospholipid PTM (Croda) | 0-1.0 |
| Farnesol/Bisabolol | 0.3-1.0 |
| Dehyquart-CA surfactant | 0.5-2.0 |
| Benzoic acid | 0.02-2.0 |
| Glucopon | 0.5-3.0 |
| Silicone (silsurf) | 0.5-2.0 |
| Adjust pH = 4.0-4.5 | |

A non-limiting specific example of an aqueous botanical hand disinfectant foam containing benzyl alcohol and botanicals of the present application includes the following formulation.

| Aqueous Botanical Hand Disinfectant Foam A 1 | |
|---|---|
| Ingredients | % w/w |
| Water | 78.75 |
| Hydroxypropyl methyl-cellulose stearoxy ether (Sangelose) | 0.1 |
| Allantoin | 0.3 |
| Grapefruit seed extract | 0.5 |
| Solubulizer (Peg-40 hydrogenated Castor oil, Trideceth 9, water) | 2.0 |
| SDA-40 B (natural) | 10 |
| Benzyl alcohol | 1.0 |
| Pentylene glycol | 1.0 |
| Phenoxyethanol | 1.0 |
| Aloe leaf juice | 0.5 |
| Bisabolol | 0.05 |
| Linalool | 0.1 |
| Lemongrass oil | 0.2 |
| Thymol | 0.1 |
| Phospholipid PTM (Croda) | 0.5 |
| Farnesol/Bisabolol | 0.5 |
| Dehyquart-CA surfactant | 0.5 |
| Benzoic acid | 0.2 |
| Glucopon | 1.3 |
| Silicone (silsurf) | 1.4 |
| Adjust pH = 4.0-4.5 | |

A non-limiting general example of an aqueous botanical hand disinfectant foam containing benzyl alcohol and botanicals of the present application includes the following formulation.

| Aqueous Botanical hand Disinfectant Foam 2 | |
|---|---|
| Ingredients | Range (% w/w) |
| Water | 54.7-90.8 |
| Kytamer (Chitosan complex) | 0.05-0.4 |
| Allantoin | 0.2-0.5 |
| Solubulizer (Peg-40 hydrogenated Castor oil, Trideceth 9, water) | 1-3 |
| SDA-40 B (natural) | 5.0-20 |
| Benzyl alcohol | 0.1-2.0 |
| Phenylethanol | 0.1-1.0 |
| *Aloe* leaf juice | 0.05-2.0 |
| Bisabolol | 0.025-0.1 |
| Lemongrass oil | 0.02-2.0 |
| Thymol | 0.05-0.2 |
| Benzoic acid | 0.02-2.0 |
| Cinnamon oil | 0.01-1.0 |
| Oregano oil | 0.01-1.0 |
| Bergamot oil | 0.01-1.0 |
| Plantasol (Caprylyl capryl glucoside) | 0.01-2.0 |
| Biowax (PEG-8 dimethicone) | 0.01-2.0 |

Adjust pH = 4.0-4.5

A non-limiting specific example of an aqueous botanical hand disinfectant foam containing benzyl alcohol and botanicals of the present application includes the following formulation.

| Aqueous Botanical hand Disinfectant Foam 2 | |
|---|---|
| Ingredients | % w/w |
| Water | 74.83 |
| Kytamer (Chitosan complex) | 0.05 |
| Allantoin | 0.2 |
| Solubulizer (Peg-40 hydrogenated Castor oil, Trideceth 9, water) | 1.5 |
| SDA-40 B (natural) | 20 |
| Benzyl alcohol | 1.0 |
| Phenylethanol | 0.3 |
| *Aloe* leaf juice | 0.5 |
| Bisabolol | 0.05 |
| Lemongrass oil | 0.1 |
| Thymol | 0.1 |
| Benzoic acid | 0.2 |
| Cinnamon oil | 0.07 |
| Oregano oil | 0.07 |
| Bergamot oil | 0.03 |
| Plantasol (Caprylyl capryl glucoside) | 0.5 |
| Biowax (PEG-8 dimethicone) | 0.5 |

Adjust pH = 4.0-4.5

The present subject matter also provides for natural alcohol foam hand disinfectants containing benzyl alcohol and botanicals. A non-limiting general example of such a formulation includes the following.

| Natural Alcohol Foam Hand Disinfectant | |
|---|---|
| Ingredients | Range (% w/w) |
| Water | 15-30 |
| Hydroxypropyl methyl-cellulose stearoxy ether (Sangelose) | 0.05-0.2 |
| Allantoin | 0.2-0.5 |
| *Wasabi* extract | 0.3-1.0 |
| Grapefruit seed extract | 0.0-1.0 |
| Honeysuckle extract | 0.0-1.0 |
| Corn derived SDA-40 B (natural) | 60.0-75.0 |
| Lemongrass oil | 0.05-1.0 |
| Veg. Glycerin | 0.5-3.0 |
| Benzyl alcohol | 0.5-3.0 |
| Benzoic acid | 0.05-1.0 |
| Bisabolol | 0.02-0.5 |
| Symsitive | 0.05-1.0 |
| Phenylethanol | 0.1-2.0 |
| Zemea (1,3-Propane diol) | 0.05-3.0 |
| Farnesol | 0.05-2.0 |
| *Aloe* leaf juice | 0.5-2.0 |
| Dow Corning 190 | 0.1-2.0 |
| Ultrapure MFB-10 | 0.5-3.0 |

A non-limiting specific example of a natural alcohol foam hand disinfectant containing benzyl alcohol and botanicals of the present application includes the following formulation.

| Natural Alcohol Foam Hand Disinfectant | |
|---|---|
| Ingredients | % w/w |
| Water | 23.2 |
| Hydroxypropyl methyl-cellulose stearoxy ether (Sangelose) | 0.05 |
| Allantoin | 0.3 |
| *Wasabi* extract | 0.3 |
| Corn derived SDA-40 B (natural) | 67 |
| Lemongrass oil | 0.2 |
| Veg. Glycerin | 2.0 |
| Benzyl alcohol | 1.0 |
| Benzoic acid | 0.2 |
| Bisabolol | 0.05 |
| Symsitive | 0.2 |
| Phenyl ethanol | 0.7 |
| Zemea (1,3-Propane diol) | 1.0 |
| Farnesol | 0.3 |
| *Aloe* leaf juice | 0.5 |
| Dow Corning 190 | 1.0 |
| Ultrapure MFB-10 | 2.0 |

A non-limiting general example of a natural alcohol foam hand disinfectant containing benzyl alcohol and botanicals of the present application includes the following formulation.

| Natural Alcohol Foam Hand Disinfectant 1 | |
|---|---|
| Ingredients | Range (% w/w) |
| Water | 15-30 |
| Kytamer (Chitosan complex) | 0.05-0.4 |
| Allantoin | 0.2-0.5 |
| *Wasabi* extract | 0.3-1.0 |
| Pluronic | 0.0-1.0 |
| Corn derived SDA-40 B (natural) | 60.0-75.0 |
| Lemongrass oil | 0.05-1.0 |
| Veg. Glycerin | 0.5-3.0 |
| Benzyl alcohol | 0.5-3.0 |
| Benzoic acid | 0.05-1.0 |
| Bisabolol | 0.02-0.5 |
| Phenyl ethanol | 0.1-2.0 |
| Zemea (1,3-Propane diol) | 0.05-3.0 |
| Farnesol | 0.05-2.0 |
| *Aloe* leaf juice | 0.5-2.0 |
| Cinnamon oil | 0.05-1.0 |

Natural Alcohol Foam Hand Disinfectant 1 -continued

| Ingredients | Range (% w/w) |
| --- | --- |
| Dow Corning 190 | 0.1-2.0 |
| PEG 10 dimethicone (Ultrapure MFB-10) | 0.5-3.0 |

A non-limiting specific example of a natural alcohol foam hand disinfectant containing benzyl alcohol and botanicals of the present application includes the following formulation.

Natural Alcohol Foam Hand Disinfectant 1

| Ingredients | % w/w |
| --- | --- |
| Water | 22.3 |
| Kytamer (Chitosan complex) | 0.05 |
| Allantoin | 0.2 |
| *Wasabi* extract | 0.3 |
| Pluronic | 0.3 |
| Corn derived SDA-40 B (natural) | 67 |
| Lemon grass oil | 0.2 |
| Veg. Glycerin | 2.0 |
| Benzyl alcohol | 1.0 |
| Benzoic acid | 0.2 |
| Bisabolol | 0.05 |
| Phenyl ethanol | 1.0 |
| Zemea (1,3-Propane diol) | 1.0 |
| Farnesol | 0.3 |
| *Aloe* leaf juice | 1.0 |
| Cinnamon leaf oil | 0.1 |
| Dow Corning 190 | 1.0 |
| PEG 10 dimethicone (Ultrapure MFB-10) | 2.0 |

The present subject matter also provides for natural alcohol surgical hand disinfectants containing benzyl alcohol and botanicals. A non-limiting general example of such a formulation includes the following.

Natural Alcohol Surgical Hand Disinfectant

| Ingredients | Range (% w/w) |
| --- | --- |
| Water | 5.0-30.0 |
| Hydroxypropyl methyl-cellulose stearoxy ether (Sangelose) | 0.05-0.2 |
| Allantoin | 0.2-0.5 |
| *Wasabi* extract | 0.1-1.0 |
| Corn derived SDA-40 B (natural) | 70.0-85.0 |
| Lemongrass oil | 0.05-1.0 |
| Veg. Glycerin | 0.5-3.0 |
| Benzyl alcohol | 0.5-3.0 |
| Lactic acid | 0.05-1.0 |
| Farnesol | 0.05-2.0 |
| Sensiva (Ethylhexyl glycerin) | 0.05-3.0 |
| Bisabolol | 0.05-0.5 |
| Symsitive | 0.05-1.0 |
| Phenylethanol | 0.1-2.0 |
| Zemea (1,3-Propanediol) | 0.05-3.0 |
| *Aloe* leaf juice | 0.5-2.0 |

A non-limiting specific example of a natural alcohol surgical hand disinfectant containing benzyl alcohol and botanicals of the present application includes the following formulation.

Natural Alcohol Surgical Hand Disinfectant

| Ingredients | % w/w |
| --- | --- |
| Water | 11.6 |
| Hydroxypropyl methyl-cellulose stearoxy ether (Sangelose) | 0.05 |
| Allantoin | 0.3 |
| *Wasabi* extract | 0.3 |
| Corn derived SDA-40 B (natural) | 79 |
| Lemongrass oil | 0.05 |
| Veg. Glycerin | 2.0 |
| Benzyl alcohol | 1.0 |
| Lactic acid | 0.2 |
| Farnesol | 1.0 |
| Sensiva (Ethylhexyl glycerin) | 2.0 |
| Bisabolol | 0.1 |
| Symsitive | 0.2 |
| Phenylethanol | 0.7 |
| Zemea (1,3-Propanediol) | 1.0 |
| *Aloe* leaf juice | 0.5 |

The present subject matter also provides for botanical disinfectant soaps containing benzyl alcohol and botanicals. A non-limiting general example of such a formulation includes the following.

Botanical Disinfectant Soap A

| Ingredients | Range (% w/w) |
| --- | --- |
| Water | 33.5-83 |
| Pluronic F-87 prill | 0.5-1.0 |
| Methocel E4 M | 0.1-0.5 |
| PolyoxWSR 205 | 0.1-0.5 |
| Glucopon | 2.0-3.0 |
| Dow corning 190 silicone surfactant | 0.5-3.0 |
| Cocoamido propyl Betaine | 0-5.0 |
| SDA 40 B alcohol | 10-20 |
| Lemongrass oil | 0.05-2.0 |
| Orange oil | 0.01-0.5 |
| Benzyl alcohol | 0.5-3.0 |
| Honeysuckle extract | 0.1-2.0 |
| Lactic acid | 0.1-2.0 |
| SDA 40 B | 2-20 |
| Veg. Glycerin | 0.5-2.0 |
| *Aloe* leaf juice | 0.5-2.0 |

A non-limiting specific example of a botanical disinfectant soap containing benzyl alcohol and botanicals of the present application includes the following formulation.

Botanical Disinfectant Soap A

| Ingredients | % w/w |
| --- | --- |
| Water | 61.0 |
| Pluronic F-87 prill | 1.00 |
| Methocel E4 M | 0.2 |
| PolyoxWSR 205 | 0.3 |
| Glucopon | 2.0 |
| Dow corning 190 silicone surfactant | 1.0 |
| Cocoamido propyl Betaine | 3.0 |
| SDA 40 B alcohol | 15.0 |
| Lemongrass oil | 0.2 |
| Orange oil | 0.1 |
| Benzyl alcohol | 2.0 |
| Honeysuckle extract | 0.5 |
| Lactic acid | 0.2 |
| SDA 40 B | 12 |
| Veg. Glycerin | 1.0 |
| *Aloe* leaf juice | 0.5 |

A non-limiting general example of a botanical disinfectant soap containing benzyl alcohol and botanicals of the present application includes the following formulation.

| Botanical Disinfectant Soap B | |
|---|---|
| Ingredients | Range (% w/w) |
| Water | 32.5-82.7 |
| Pluronic F-87 prill | 0.5-1.0 |
| Methocel E4 M | 0.1-0.5 |
| PolyoxWSR 205 | 0.1-0.5 |
| Glucopon | 2.0-3.0 |
| Dow corning 190 silicone surfactant | 0.5-3.0 |
| Cocoamido propyl Betaine | 0-5.0 |
| SDA 40 B alcohol | 10-20 |
| Lemongrass oil | 0.05-2.0 |
| Orange oil | 0.01-0.5 |
| Benzyl alcohol | 0.5-3.0 |
| *Wasabi* extract | 0.1-2.0 |
| Farnesol | 0.3-1.0 |
| Lactic acid | 0.1-2.0 |
| SDA 40 B | 2-20 |
| Veg. Glycerin | 0.5-2.0 |
| *Aloe* leaf juice | 0.5-2.0 |

A non-limiting specific example of a botanical disinfectant soap containing benzyl alcohol and botanicals of the present application includes the following formulation.

| Botanical Disinfectant Soap B | |
|---|---|
| Ingredients | % w/w |
| Water | 60.5 |
| Pluronic F-87 prill | 1.00 |
| Methocel E4 M | 0.2 |
| PolyoxWSR 205 | 0.3 |
| Glucopon | 2.0 |
| Dow corning 190 silicone surfactant | 1.0 |
| Cocoamido propyl Betaine | 3.0 |
| SDA 40 B alcohol | 15.0 |
| Lemongrass oil | 0.2 |
| Orange oil | 0.1 |
| Benzyl alcohol | 2.0 |
| *Wasabi* extract | 0.5 |
| Farnesol | 0.5 |
| Lactic acid | 0.2 |
| SDA 40 B | 12 |
| Veg. Glycerin | 1.0 |
| *Aloe* leaf juice | 0.5 |

A non-limiting general example of a botanical disinfectant soap containing benzyl alcohol and botanicals of the present application includes the following formulation.

| Botanical Disinfectant Soap | |
|---|---|
| Ingredients | Range (% w/w) |
| Water | 50-93.0 |
| Pluronic F-87 prill | 0.5-1.0 |
| Methocel E4 M | 0.1-0.5 |
| PolyoxWSR 205 | 0.1-0.5 |
| Glucopon | 2.0-3.0 |
| Dow corning 190 silicone surfactant | 0.5-3.0 |
| Cocoamido propyl Betaine | 0-5.0 |
| Lemongrass oil | 0.05-2.0 |
| Orange oil | 0.01-0.5 |
| Benzyl alcohol | 0.5-3.0 |
| Honeysuckle extract | 0.1-2.0 |
| Lactic acid | 0.1-2.0 |
| SDA 40 B | 2-20 |
| Veg. Glycerin | 0.5-2.0 |
| *Aloe* leaf juice | 0.5-2.0 |

A non-limiting specific example of a botanical disinfectant soap containing benzyl alcohol and botanicals of the present application includes the following formulation.

| Botanical Disinfectant Soap | |
|---|---|
| Ingredients | % w/w |
| Water | 76.0 |
| Pluronic F-87 prill | 1.00 |
| Methocel E4 M | 0.2 |
| PolyoxWSR 205 | 0.3 |
| Glucopon | 2.0 |
| Dow corning 190 silicone surfactant | 1.0 |
| Cocoamido propyl Betaine | 3.0 |
| Lemongrass oil | 0.2 |
| Orange oil | 0.1 |
| Benzyl alcohol | 2.0 |
| Honeysuckle extract | 0.5 |
| Lactic acid | 0.2 |
| SDA 40 B | 12 |
| Veg. Glycerin | 1.0 |
| *Aloe* leaf juice | 0.5 |

In certain non-limiting embodiments, an anti-fungal, anti-itch composition is provided comprising from about 0.5% (w/w) to about 5% (w/w) benzyl alcohol and one or more compounds selected from the group consisting of:

(a) from about 0.04% (w/w) to about 0.5% (w/w) botanical extract selected from the group consisting of wasabi extract, honeysuckle extract, cedar wood extract, aspen bark extract, willow bark extract, Brahmi extract and combinations thereof;

(b) from about 0.04% (w/w) to about 1.05% (w/w) essential oil selected from the group consisting of lemongrass oil, cinnamon oil, oregano oil, thymol, galangal oil, orange oil, pomegranate oil, calendula oil, curry leaf oil or combinations thereof; and (c) from about 0.2% (w/w) to about 2.0% (w/w) natural organic acid.

In certain non-limiting embodiments, an anti-fungal, anti-itch composition is provided, as follows:

| Ingredient | Range (% w/w) |
|---|---|
| White Petrolatum* | 4-6 |
| Stearyl Alcohol | 13-17 |
| Isopropyl Myristate | 5-7 |
| Sorbitan Oleate | 2-3 |
| Polyoxyl 40 Stearate(Myrj 52) | 5-7 |
| Water | 50-60 |
| Germall+ | 0.1-0.3 |
| Propylene glycol | 2-4 |
| Lactic acid | 0.01-0.1 |
| Zinc oxide | 0.5-2.0 |
| *Calendula* oil | 0.5-1.0 |
| Oat powder | 1.0-2.0 |
| Brahmi extract | 0.5-1.0 |
| Resveratrol | 0.3-1.0 |
| Tetrahydrocurcuminoid | 0.05-0.1 |
| Benzyl alcohol | 0.01-0.1 |

A non-limiting general example of an alcohol-free botanical hand disinfectant lotion containing benzyl alcohol and botanicals of the present application, where a Phase A solution and a Phase B solution are first prepared separately and then mixed, includes the following formulation.

| Alcohol-free Botanical Hand Disinfectant Lotion | |
| --- | --- |
| Ingredients | Range(% w/w) |
| PHASE A | |
| Water | 70-87 |
| Allantoin | 0.1-0.5 |
| Methocel E4 M | 0.1-0.5 |
| Hydroxypropyl methyl-cellulose stearoxy ether (Sangelose) or Kytomer | 0.05-0.2 |
| Cetrimonium chloride | 0.3-0.7 |
| Propylene glycol | 0.5-2.0 |
| Glycerin | 1-5 |
| Heat 50-60° C. | |
| Incroquat TMS | 0.5-2.0 |
| Polowax NF | 0.5-2.0 |
| Stearyl alcohol | 0.5-2.0 |
| Zinc oxide | 0.2-0.5 |
| Silicone fluid (Dimethicone200/350) | 1-3.0 |
| *Aloe* juice | 0.5-2.0 |
| Bisabolol | 0.05-0.2 |
| Phase B | |
| Benzyl alcohol | 0.5-2.0 |
| Thymol | 0.05-0.2 |
| Cinnamon oil | 0.05-0.1 |
| Lemongrass oil | 0.1-0.2 |
| Pomegranate oil | 0.2-0.4 |
| Oregano oil | 0.05-0.2 |
| Lemon Extract | 0.2-0.5 |
| Bergamot | 0.03-0.05 |
| Lactic acid | 0.1-0.2 |

A non-limiting specific example of an alcohol-free botanical hand disinfectant lotion containing benzyl alcohol and botanicals of the present application, where a Phase A solution and a Phase B solution are first prepared separately and then mixed, includes the following formulation.

| Alcohol-free Botanical Hand Disinfectant Lotion | |
| --- | --- |
| Ingredients | % w/w |
| PHASE A | |
| Water | 87.45 |
| Allantoin | 0.3 |
| Methocel E4 M | 0.2 |
| Hydroxypropyl methyl-cellulose stearoxy ether (Sangelose) or Kytomer | 0.1 |
| Cetrimonium chloride | 0.5 |
| Propylene glycol | 1.0 |
| Glycerin | 3.0 |
| Heat 50-60° C. | |
| Incroquat TMS | 1.5 |
| Polowax NF | 0.5 |
| Stearyl alcohol | 0.5 |
| Zinc oxide | 0.3 |
| Silicone fluid (Dimethicone200/350) | 2.0 |
| *Aloe* juice | 0.5 |
| Bisabolol | 0.05 |
| Phase B | |
| Benzyl alcohol | 1.0 |
| Thymol | 0.2 |
| Cinnamon leaf oil | 0.1 |
| Lemongrass oil | 0.1 |
| Pomegranate oil | 0.2 |
| Oregano oil | 0.1 |
| Lemon Extract | 0.3 |
| Bergamot | 0.05 |
| Lactic acid | 0.2 |

A non-limiting general example of an alcohol-free botanical hand disinfectant foam of the present application includes the following formulation.

| Alcohol-free Botanical hand Disinfectant Foam | |
| --- | --- |
| Ingredients | Range % (w/w) |
| Water | 85-90 |
| Kytamer (Chitoson complex) | 0.05-0.2 |
| Allantoin | 0.1-0.3 |
| Solubulizer (Peg-40 hydrogented Castor oil, Trideceth 9, water) | 1-4 |
| Benzyl alcohol | 0.5-2.0 |
| Benzoic acid | 0.1-0.3 |
| Phenylethanol | 0.2-0.5 |
| *Aloe* leaf juice | 0.5-2.0 |
| Bisabolol | 0.05-0.21 |
| Lemon grass oil | 0.1-0.2 |
| Thymol | 0.05-0.2 |
| Cinnamon oil | 0.05-0.1 |
| Oregano oil | 0.05-0.1 |
| Lemon extract | 0.2-0.5 |
| Lactic acid | 0.2 |
| Plantasol (Caprylyl capryl glucoside) | 0.5-1.0 |
| Biowax (PEG-8 dimethicone) | 0.25-1.0 |
| Coco amido propyl betaine | 0.5-2.0 |

Adjust pH = 4.0-4.5

A non-limiting specific example of an alcohol-free botanical hand disinfectant foam of the present application includes the following formulation.

| Alcohol-free Botanical hand Disinfectant Foam | |
| --- | --- |
| Ingredients | % w/w |
| Water | 92.3 |
| Kytamer (Chitoson complex) | 0.05 |
| Allantoin | 0.2 |
| Solubulizer (Peg-40 hydrogented Castor oil, Trideceth 9, water) | 3.0 |
| Benzyl alcohol | 1.0 |
| Benzoic acid | 0.2 |
| Phenylethanol | 0.3 |
| *Aloe* leaf juice | 0.5 |
| Bisabolol | 0.05 |
| Lemon grass oil | 0.1 |
| Thymol | 0.1 |
| Cinnamon leaf oil | 0.10 |
| Oregano oil | 0.10 |
| Lemon extract | 0.3 |
| Lactic acid | 0.2 |
| Plantasol (Caprylyl capryl glucoside) | 0.5 |
| Biowax (PEG-8 dimethicone) | 0.5 |
| Coco amido propyl betaine | 0.5 |

Adjust pH = 4.0-4.5

4.14 Wound Healing

The compositions of the present subject matter may be used to promote wound healing and/or to inhibit surface infections. In various non-limiting embodiments, the compositions of the present subject matter may be utilized in products such as topical creams and lotions, wound care products, burn wound cream, decubitous ulcer cream (with anti-Active inflammatory botanicals and the use of silver sulfadiazene as an anti-microbial agent), and therapeutic ointments. The compositions of the present subject matter may also be applied to wound care items, such as, but not limited to, wound healing ointments, wound coverings, burn wound cream, bandages, tape, and steri-strips, and medical articles such as medical gowns, caps, face masks, and shoe-covers, surgical drops, etc.

In various non-limiting embodiments, a composition may comprise a thickening and/or gelling agent such as stearyl alcohol, cationic hydroxy ethyl cellulose (Ucare; JR30), hydroxy propyl methyl cellulose, hydroxy propyl cellulose (Klucel), chitosan pyrrolidone carboxylate (Kytamer), behenyl alcohol, zinc stearate, emulsifying waxes, including but not limited to Incroquat and Polawax, an addition polymer of acrylic acid, a resin such as Carbopol® ETD™ 2020, guar gum, acacia, acrylates/steareth-20 methacrylate copolymer, agar, algin, alginic acid, ammonium acrylate co-polymers, ammonium alginate, ammonium chloride, ammonium sulfate, amylopectin, attapulgite, bentonite, C9-15 alcohols, calcium acetate, calcium alginate, calcium carrageenan, calcium chloride, caprylic alcohol, carbomer 910, carbomer 934, carbomer 934P, carbomer 940, carbomer 941, carboxymethyl hydroxyethyl cellulose, carboxymethyl hydroxypropyl guar, carrageenan, cellulose, cellulose gum, cetearyl alcohol, cetyl alcohol, corn starch, damar, dextrin, dibenzlidine sorbitol, ethylene dihydrogenated tallowamide, ethylene diolamide, ethylene distearamide, gelatin, guar gum, guar hydroxypropyltrimonium chloride, hectorite, hyaluronic acid, hydrated silica, hydroxybutyl methylcellulose, hydroxyethylcellulose, hydroxyethyl ethylcellulose, hydroxyethyl stearamide-MIPA, isocetyl alcohol, isostearyl alcohol, karaya gum, kelp, lauryl alcohol, locust bean gum, magnesium aluminium silicate, magnesium silicate, magnesium trisilicate, methoxy PEG-22/dodecyl glycol copolymer, methylcellulose, microcrystalline cellulose, montmorillonite, myristyl alcohol, oat flour, oleyl alcohol, palm kernel alcohol, pectin, PEG-2M, PEG-5M, polyacrylic acid, polyvinyl alcohol, potassium alginate, potassium aluminium polyacrylate, potassium carrageenan, potassium chloride, potassium sulfate, potato starch, propylene glycol alginate, sodium acrylate/vinyl alcohol copolymer, sodium carboxymethyl dextran, sodium carrageenan, sodium cellulose sulfate, sodium chloride, sodium polymethacylate, sodium silicoaluminate, sodium sulfate, stearalkonium bentotnite, stearalkonium hectorite, stearyl alcohol, tallow alcohol, TEA-hydrochloride, tragacanth gum, tridecyl alcohol, tromethamine magnesium aluminium silicate, wheat flour, wheat starch, xanthan gum, abietyl alcohol, acrylinoleic acid, aluminum behenate, aluminum caprylate, aluminum dilinoleate, aluminum salts, such as distearate, and aluminum isostearates, beeswax, behenamide, butadiene/acrylonitrile copolymer, C29-70 acid, calcium behenate, calcium stearate, candelilla wax, carnauba, ceresin, cholesterol, cholesterol hydroxystearate, coconut alcohol, copal, diglyceryl stearate malate, dihydroabietyl alcohol, dimethyl lauramine oleate, dodecanoic acid/cetearyl alcohol/glycol copolymer, erucamide, ethylcellulose, glyceryl triacetyl hydroxystearate, glyceryl tri-acetyl ricinolate, glycol dibehenate, glycol di-octanoate, glycol distearate, hexanediol distearate, hydrogenated C6-14 olefin polymers, hydrogenated castor oil, hydrogenated cottonseed oil, hydrogenated lard, hydrogenated menhaden oil, hydrogenated palm kernel glycerides, hydrogenated palm kernel oil, hydrogenated palm oil, hydrogenated polyisobutene, hydrogenated soybean oil, hydrogenated tallow amide, hydrogenated tallow glyceride, hydrogenated vegetable glyceride, hydrogenated vegetable oil, Japan wax, jojoba wax, lanolin alcohol, shea butter, lauramide, methyl dehydroabietate, methyl hydrogenated rosinate, methyl rosinate, methylstyrene/vinyltoluene copolymer, microcrystalline wax, montan acid wax, montan wax, myristyleicosanol, myristyloctadecanol, octadecene/maleic anhyrdine copolymer, octyldodecyl stearoyl stearate, oleamide, oleostearine, ouricury wax, oxidized polyethylene, ozokerite, paraffin, pentaerythrityl hydrogenated rosinate, pentaerythrityl tetraoctanoate, pentaerythrityl rosinate, pentaerythrityl tetraabietate, pentaerythrityl tetrabehenate, pentaerythrityl tetraoleate, pentaerythrityl tetrastearate, ophthalmic anhydride/glycerin/glycidyl decanoate copolymer, ophthalmic/trimellitic/glycols copolymer, polybutene, polybutylene terephthalate, polydipentene, polyethylene, polyisobutene, polyisoprene, polyvinyl butyral, polyvinyl laurate, propylene glycol dicaprylate, propylene glycol dicocoate, propylene glycol diisononanoate, propylene glycol dilaurate, propylene glycol dipelargonate, propylene glycol distearate, propylene glycol diundecanoate, PVP/eiconsene copolymer, PVP/hexadecene copolymer, rice bran wax, stearlkonium bentonite, stearalkonium hectorite, stearamide, stearamide DEA-distearate, stearamide DIBA-stearate, stearamide MEA-stearate, stearone, stearyl erucamide, stearyl stearate, stearyl stearoyl stearate, synthetic beeswax, synthetic wax, trihydroxystearin, triisononanoin, triisostearin, tri-isostearyl trilinoleate, trilaurin, trilinoleic acid, trilinolein, trimyristin, triolein, tripalmitin, tristearin, zinc laurate, zinc myristate, zinc neodecanoate, zinc rosinate, and mixtures thereof. The gelling agents used in vehicles may be natural gelling agents such as natural gums, starches, pectins, agar and gelatin. Often, the gelling agents are based on polysaccharides or proteins Examples include but are not limited to guar gum, Xanthum gum, Alginic acid (E400), sodium alginate (E401), potassium alginate (E402), ammonium alginate (E403), calcium alginate (E404,—polysaccharides from brown algae), Agar (E406, a polysaccharide obtained from red seaweeds), Carrageenan (E407, a polysaccharide obtained from red seaweeds), Locust bean gum (E410, a natural gum from the seeds of the Carob tree), Pectin (E440, a polysaccharide obtained from apple or citrus-fruit), and Gelatin (E441, made by partial hydrolysis of animal collagen).

Various embodiments may comprise a stabilizer. In a non-limiting example, sodium perborate is used as the stabilizing agent in an amount ranging from about 0.3 to about 1% w/w.

Various embodiments of the application may further comprise a surfactant. The surfactant may be an anionic surfactant, a cationic surfactant, an ampholytic surfactant, or a nonionic surfactant. Examples of nonionic surfactants include polyethoxylates, fatty alcohols (e.g., ceteth-20 (a cetyl ether of polyethylene oxide having an average of about 20 ethylene oxide units) and other "BRIJ®" nonionic surfactants available from ICI Americas, Inc. (Wilmington, Del.)), cocamidopropyl betaine, alkyl phenols, fatty acid esters of sorbitol, sorbitan, or polyoxyethylene sorbitan. Suitable anionic surfactants include ammonium lauryl sulfate and lauryl ether sulfosuccinate. Preferred surfactants include lauroyl ethylenediamine triacetic acid sodium salt, Pluronic F87, Masil SF-19 (BASF) and incromide.

Water used in the formulations described herein is preferably deionized water having a neutral pH.

In specific non-limiting embodiments, the present subject matter provides for a wound healing topical cream containing silver sulfadiazine, an insoluble zinc salt, a soluble zinc salt and calendula oil. In another non-limiting embodiment, the present subject matter provides for a wound healing topical cream containing silver sulfadiazine, an insoluble zinc salt, a soluble zinc salt, calendula oil, and anti inflammatory agents such as a curcumin compound.

Non-limiting examples of cream products may further contain white petrolatum (2-20%), fatty alcohol (2-20%), emollient (1-10%), emulsifying agent (0.5-10%), humectant (2-15%), preservative (0.1-0.5%), and deionized or distilled water q.s. 100%. Fatty alcohols include stearyl, alcohol, cetyl alcohol, lauryl alcohol, myristyl alcohol, and other known fatty alcohols. Emollients include isopropyl myristate, lanolin, lanolin derivatives, isopropyl palmitate, isopropyl stearate, emu oil, linseed oil and other known emollients. Emulsifying agents include sodium mono-oleate and polyoxyl 40 stearate. Humectants include propylene glycol, sorbitol, or glycerine or mixture thereof. Suitable water soluble preservatives include parabens, sorbic acid, benzoic acid, diazolidinyl urea, and iodopropylbutylcarbamate (Germal+).

The present subject matter provides for botanical wound healing gel formulation comprising benzyl alcohol and botanicals. A non-limiting general example of such a formulation includes the following.

| Botanical Wound Healing Gel | |
|---|---|
| Ingredients | Range (% w/w) |
| *Echinacea purpuria* extract | 0.1-1.0 |
| Pomegranate oil | 0.1-1.0 |
| Rosemary oil | 0.1-1.0 |
| Lemongrass oil | 0.1-0.5 |
| Cinnamon oil | 0-0.5 |
| Thymol | 0.05-0.2 |
| Benzoic acid | 0.2-0.5 |
| Sodium Benzoate | 0.2-0.5 |
| Curcumin | 0.05-0.7 |
| Oatmeal | 0.5-5.0 |
| Ascorbic acid (Vitamin C) | 0.5-2.0 |
| *Calendula* Oil | 0.3-1.0 |
| Benzyl alcohol | 0.1-0.5 |
| Zinc Oxide | 0.2-1.0 |
| Zinc stearate | 0.2-1.0 |
| Glycerin | 5.0-20.0 |
| Buckthorn oil | 0-0.5 |
| Virgin coconut oil | 0-2.0 |
| Almond oil | 0.1-1.0 |
| Emu oil | 0-2.0 |
| Water | 54.1-91.9 |
| *Aloe* gel | 0.25-5.0 |
| Hydroxypropylmethyleellulose and derivatives | 0.1-1.0 |

Adjust pH to 5.0-6.0

A non-limiting specific example of a botanical wound healing gel formulation containing benzyl alcohol and botanicals of the present application includes the following formulation.

| Botanical Wound Healing Gel | |
|---|---|
| Ingredients | % w/w |
| *Echinacea purpuria* extract | 0.3 |
| Pomegranate oil | 0.3 |
| Rosemary oil | 0.3 |
| Lemongrass oil | 0.1 |
| Cinnamon oil | 0.2 |
| Thymol | 0.1 |
| Benzoic acid | 0.2 |
| Sodium Benzoate | 0.2 |
| Curcumin | 0.5 |
| Oatmeal | 1.0 |
| Ascorbic acid (Vitamin C) | 1.0 |
| *Calendula* Oil | 0.5 |
| Benzyl alcohol | 0.5 |
| Zinc Oxide | 0.3 |
| Zinc stearate | 0.3 |
| Glycerin | 10.0 |
| Buckthorn oil | 0.3 |
| Virgin coconut oil | 1.0 |
| Almond oil | 0.3 |
| Water | 80.3 |
| *Aloe* gel | 2.0 |
| Hydroxypropylmethylcellulose and derivatives | 0.3 |

Adjust pH to 5.0-6.0

4.15 Veterinary Products

In a subset of non-limiting embodiments, the present subject matter provides for veterinary products for care of any domestic animal, including but not limited to cats, dogs, birds, rodents, rabbits, horses, cows and cattle, sheep, goats, etc.

Non-limiting examples of veterinary care products which may utilize the compositions of the present subject matter include pet shampoo, pet cleansing wipes including body wipes, ear wipes, and eye wipes, dental wipes, toothpaste, ear cleaning liquid, cage cleaner, surface cleaner for housebreaking accidents, topical creams, ointments, teat dip therapeutic for mastitis and liquid to be applied to pet's skin (as in a "body splash").

Veterinary care compositions according to the application may further comprise one or (preferably) more than one component selected from the group consisting of emollients, stabilizing agents, thickening agents, humectants, antimicrobial agents, neutralizing agents, surfactants, water, silicone polymers, alcohols, and hydrogels, anti-inflammatory agents, wound healing agents, salicylic acid, as well as additional components as may be known in the art.

Specific, non-limiting examples of additional components which may be comprised in pet care products include the components listed above for personal care products.

In certain non-limiting embodiments of the application, the compositions may be prepared for teat dip to treat mastitis. The anti-irritants used for teat dip may include but are not limited to zinc salts with panthenol, or Bisabolol with ginger root extract (symrelief), or symrelief with a zinc salt. The gelling agents in the vehicle may include but are not limited to natural gelling agents such as natural gums, starches, pectins, agar and gelatin. Antimicrobial botanicals may include but are not limited to lemongrass oil, orange oil and fruit acids such as citric and lactic acid, phenoxyethanol (constituent of sage oil).

4.16 Household/Industrial Products

In a subset of non-limiting embodiments, the present subject matter provides for household/industrial products comprising the formulations outlined above.

Non-limiting embodiments of household/industrial products which may utilize the compositions of the present subject matter include householder cleaners such as concentrated liquid cleaners and spray cleaners, cleaning wipes, dish washing liquid, dish washer detergent, spray-mop liquid, furniture polish, indoor paint, outdoor paint, dusting spray, laundry detergent, fabric softener, rug/fabric cleaner, window and glass cleaner, toilet bowl cleaner, liquid/cream cleanser, etc. In a particular embodiment, the compositions of the present subject matter may be used in a food wash product, designed to clean fruits and vegetables prior to consumption. "Household products" are products, other than personal care products, that would be used by individual consumers. "Industrial products" refers to products that are used in industry.

Household-industrial compositions according to the application may comprise one or more component selected from the group consisting of surfactants, builders (e.g., sequestering builders, precipitating builders, ion exchange builders), solvents, thickeners, abrasives, acids, bases (alkalis), antimicrobial agents, soaps, bleaching agents, enzymes, preservatives, and sudsing agents, as well as additional components as may be known in the art.

In various non-limiting embodiments, the compositions may comprise a surfactant, for example, but not limited to, an anionic surfactant such as an alkyl sulfate, an alkyldiphenyloxide disulfonate salt (e.g., the DOWFAX series by the Dow Chemical Company), an alkylbenzenesulfonate, an alcohol ethoxysulfate; a cationic surfactant; a non-ionic surfactant, such as a secondary alcohol ethoxylate (e.g., the TERGITAOL series by the Dow Chemical Company) or an alkyl polyglucoside (e.g., the TRITON series by the Dow Chemical Company); or an amphoteric surfactant such as an imidazoline or betaine compound.

In various non-limiting embodiments, the compositions may comprise a solvent, for example, but not limited to, water, an alcohol such as methanol, ethanol, isopropyl alcohol, or butanol; a hydrocarbon such as an aromatic hydrocarbon, propylene glycol, methylene chloride, acetone, a petroleum distillate, and/or a glycol ether.

In various non-limiting embodiments, the compositions used in a household/industrial product may comprise a thickener, for example, but not limited to, a polyethylene glycol, a methoxypolyethylene glycol, and/or hydroxyethyl cellulose.

In various non-limiting embodiments, the compositions used in a household/industrial product may comprise an abrasive, such as, but not limited to, silica, feldspar or calcite.

In various non-limiting embodiments, the compositions used in a household/industrial product may comprise an acid, such as, but not limited to, acetic acid, hydroacetic acid, phosphoric acid or hydrochloric acid.

In various non-limiting embodiments, the compositions used in a household/industrial product may comprise a base (alkali) such as, but not limited to, ammonia or sodium bicarbonate.

In various non-limiting embodiments, the compositions used in a household/industrial product may comprise an antimicrobial agent, for example, but not limited to, compounds as set forth above for personal care compositions, and also pine oil and sodium hypochlorite.

In various non-limiting embodiments, the compositions used in a household/industrial product may comprise a bleaching agent, for example, but not limited to, sodium hypochlorite, hydrogen peroxide, sodium percarbonate and sodium perborate.

In various non-limiting embodiments, the compositions used in a household/industrial product may comprise an enzyme, such as, but not limited to, a protease or a lipase.

In various non-limiting embodiments, the compositions used in a household/industrial product may comprise a preservative, such as, but not limited to, butylated hydroxytoluene, glutaraldehyde, and EDTA.

In various non-limiting embodiments, the compositions used in a household/industrial product may comprise a sudsing agent, such as, but not limited to, diethanolamine or triethanolamine.

In specific, non-limiting embodiments, the present subject matter provides for the following surface cleaners, having concentrations of active ingredients as well as concentrated stock solutions of these formulations which may be diluted to achieve the respective concentrations.

In a subset of non-limiting embodiments, the present subject matter provides for preservatives and surface disinfectants comprising the formulations outlined above.

In non-limiting embodiments, preservatives and surface disinfectants of the present subject matter include the following general formulation.

| Botanical Preservative A | |
|---|---|
| Ingredient | Range (% w/w) |
| Benzyl alcohol | 45.0-82.0 |
| Thymol | 5.0-10.0 |
| Galangal oil | 5.0-10.0 |
| Cinnamon oil | 2.0-10.0 |
| Lemongrass oil | 1.0-5.0 |
| *Wasabi* extract | 5.0-20 |

Use level is 0.20 to 1.0%

In non-limiting embodiments, preservatives and surface disinfectants of the present subject matter include the following specific formulation.

| Botanical Preservative A | |
|---|---|
| Ingredient | % w/w |
| Benzyl alcohol | 73.6 |
| Thymol | 7.4 |
| Galangal oil | 7.4 |
| Cinnamon oil | 2.9 |
| Lemongrass oil | 1.4 |
| *Wasabi* extract | 7.3 |

Use level is 0.20 to 1.0%

In non-limiting embodiments, preservatives and surface disinfectants of the present subject matter include the following general formulation.

| Botanical Surface Disinfectant A | |
|---|---|
| Ingredients | Range (% w/w) |
| Lemongrass oil | 0.5-2.5 |
| Pine oil | 0.1-1.0 |
| Glucopon 215 UP | 5-25 |
| Citric acid | 2-10 |
| SDA 3C | 2.5-35 |
| Benzyl alcohol | 2.5-27 |
| Water | 0-90 |

In non-limiting embodiments, preservatives and surface disinfectants of the present subject matter include the following specific formulation.

Botanical Surface Disinfectant A

| Ingredients | % w/w |
| --- | --- |
| Lemongrass oil | 0.5 |
| Pine oil | 0.1 |
| Glucopon 215 UP | 5.0 |
| Citric acid | 2.0 |
| SDA 3C | 7.0 |
| Benzyl alcohol | 5.4 |
| Water | 80 |

In non-limiting embodiments, preservatives and surface disinfectants of the present subject matter include the following general formulation.

Botanical Surface Disinfectant B

| Ingredients | Range (% w/w) |
| --- | --- |
| Lemongrass oil | 0.5-2.5 |
| Pine oil | 0.1-1.0 |
| Glucopon 215 UP | 5-25 |
| Citric acid | 2-10 |
| Benzyl alcohol | 10-30 |
| Water | 31.5-69.4 |

In non-limiting embodiments, preservatives and surface disinfectants of the present subject matter include the following specific formulation.

Botanical Surface Disinfectant B

| Ingredients | % w/w |
| --- | --- |
| Lemongrass oil | 0.5 |
| Pine oil | 0.1 |
| Glucopon 215 UP | 5.0 |
| Citric acid | 2.0 |
| Benzyl alcohol | 17 |
| Water | 31.5-69.4 |

In non-limiting embodiments, preservatives and surface disinfectants of the present subject matter include the following general formulation.

Hard Surface Disinfectant C

| Ingredients | Range (% w/w) |
| --- | --- |
| Sodium hypochlorite | 0.5-3.0 |
| Lemongrass oil | 0.5-2.5 |
| Pine oil | 0.1-1.0 |
| Glucopon 215 UP | 5-25 |
| Citric acid | 2-10 |
| Water | 28.5-86.9 |
| Benzyl alcohol | 5-30 |

In non-limiting embodiments, preservatives and surface disinfectants of the present subject matter include the following specific formulation.

Hard Surface Disinfectant C

| Ingredients | % w/w |
| --- | --- |
| Sodium hypochlorite | 1.0 |
| Lemongrass oil | 0.5 |
| Pine oil | 0.1 |

Hard Surface Disinfectant C

| Ingredients | % w/w |
| --- | --- |
| Glucopon 215 UP | 5.0 |
| Citric acid | 2.0 |
| Water | 81.4 |
| Benzyl alcohol | 10 |

In non-limiting embodiments, preservatives and surface disinfectants of the present subject matter include the following general formulation.

Botanical Surface Disinfectant LG-50

| Ingredients | Range (% w/w) |
| --- | --- |
| Lemongrass oil | 2.5-10.0 |
| Pine oil | 0.5-5.0 |
| Glucopon 215 UP | 25-50 |
| Citric acid | 10-20 |
| SDA 3C | 20-40 |
| Water | 20-40 |

In non-limiting embodiments, preservatives and surface disinfectants of the present subject matter include the following specific formulation.

Botanical Surface Disinfectant LG-50

| Ingredients | % w/w |
| --- | --- |
| Lemongrass oil | 2.5 |
| Pine oil | 0.5 |
| Glucopon 215 UP | 25 |
| Citric acid | 10 |
| SDA 3C | 35 |
| Water | 27 |

Botanical disinfectant Spray

| Ingredients | % (w/w) |
| --- | --- |
| Benzyl alcohol | 2-5.0 |
| Lemongrass oil | 0.3-0.5 |
| Pine oil | 0.1-0.3 |
| Thymol | 0.05-0.2 |
| Lactic acid | 1.0-2.0 |
| Citrus) Lemon) extract | 0.3-0.5 |
| SDA 40 B | 35-50 |
| Non ionic surfactant (Glueopon) | 0.3-0.7 |
| Water | 50-55 |

4.17 Medical Devices

In a subset of non-limiting embodiments, the present subject matter provides for medical devices comprising the formulations outlined above.

Implantation of a medical device produces rapid inflammatory reaction at the implantation site. This may result in the formation of a biofilm on the surface of the medical device. The biofilm on the surface of a medical device serves as a receptor for microbes resulting in microbial adhesion. Prevention of inflammation around the implanted medical device can prevent bacterial adherence on the device. This may be achieved by maintaining an inflammation and infection-free environment around the device by coating and/or impregnating the device with anti inflammatory agents and antimicrobials.

Anti-inflammatory antimicrobial compositions comprising a combination of benzyl alcohol, 1,3 propanediol and THC (with or without other antimicrobials such as chlorhexidine and silver salts) can be used to coat or impregnate medical devices such as catheters, wound dressing, soft tissue patches, etc.

4.18 Pesticides

In a subset of non-limiting embodiments, the present subject matter provides for pesticides comprising the formulations outlined above. In a non-limiting general example, pesticides of the present subject matter include the following formulation.

| Botanical Plant Pesticide | |
|---|---|
| Ingredients | Range (% w/w) |
| Benzyl alcohol | 5-20 |
| Tobacco extract | 0.01-2.0 |
| Lemongrass oil | 0.01-2.0 |
| Curry leaf oil | 0.01-2.0 |
| Cedar wood oil | 0.5-4.0 |
| Cocoamido propyl betaine | 0.5-5.0 |
| Water | 60-93.83 |
| Tea extract | 0.1-3.0 |
| Solubilizer | 0.0-2.0 |

For use, the above composition can be diluted 1 to 10 with, for example water.

In a non-limiting specific example, pesticides of the present subject matter include the following formulation.

| Botanical Plant Pesticide | |
|---|---|
| Ingredients | % w/w |
| Benzyl alcohol | 10 |
| Tobacco extract | 0.2 |
| Lemongrass oil | 1.0 |
| Curry leaf oil | 0.5 |
| Cedar wood oil | 2.0 |
| Cocoamido propyl betaine | 2.0 |
| Water | 82.8 |
| Tea extract | 0.5 |
| Solubilizer | 1.0 |

For use, the above composition can be diluted 1 to 10 with, for example water.

5. EXAMPLES

The detailed description hereby incorporates, by reference, the specific working examples of the application set forth below.

The working examples sometimes refer to Dial® soap. Dial® soap is a commercially sold liquid soap, where Dial® Antibacterial hand soap comprises, as active agent, 0.15 percent triclosan, and the inactive agents are water, sodium laureth sulfate, ammonium lauryl sulfate, decyl glucoside, cocamidopropyl betaine, glycerine, sodium chloride, PEG-18 glyceryl oleate/cocoate, fragrance, cocamide MEA, DMDM hydantoin, tetrasodium ethylene diamine tetracetic acid and colors.

Example 1

Antimicrobial Efficacy of an Aqueous Botanical Hand Disinfectant Foam A: Rapid (15 Second) and Broad Spectrum Antibacterial Efficacy The FDA TFM method (modified slightly by using lower volumes of sanitizer and microbe culture, but in the same proportion) for testing the efficacy to rapidly kill bacteria was used. The rapid antibacterial activity (15 seconds exposure) of the hand foam of the present subject matter was tested against various organisms listed in Table 1. The hand foam tested comprised the following formulation.

| Aqueous Botanical Hand Disinfectant Foam A | |
|---|---|
| Ingredients | % w/w |
| Water | 78.15 |
| Hydroxypropyl methyl-cellulose stearoxy ether (Sangelose) | 0.1 |
| Allantoin | 0.3 |
| Grapefruit seed extract | 0.5 |
| Solubulizer (Peg-40 hydrogenated Castor oil, Trideceth 9, water) | 2.0 |
| SDA-40 B (natural) | 10 |
| Benzyl alcohol | 1.0 |
| Pentylene glycol | 1.0 |
| Phenoxyethanol | 1.0 |
| Aloe leaf juice | 0.5 |
| Bisabolol | 0.05 |
| Wasabi extract | 0.3 |
| Honeysuckle extract | 0.3 |
| Linalool | 0.1 |
| Lemongrass oil | 0.2 |
| Thymol | 0.1 |
| Phospholipid PTM (Croda) | 0.5 |
| Farnesol/Bisabolol | 0.5 |
| Cationic surfactant | 0.5 |
| Benzoic acid | 0.2 |
| Glucopon | 1.3 |
| Silicone (silsurf) | 1.4 |
| Adjust pH = 4.0-4.5 | |

Method:

Briefly, hand foam (0.8 ml) was placed in a sterile culture tube and 0.2 ml of $10^9$ cfu/ml of test bacterial culture (or $10^7$ cfu/ml of *Candida* culture), diluted 1:1 with bovine adult serum, was added and mixed. After 15 s, the antimicrobial activity was stopped with drug neutralizing fluid (DNF). Serial dilutions were made with DNF, and aliquots were subcultured on trypticase soy agar to determine the number of microbial colonies per sample. For controls, phosphate buffered saline (PBS) containing the same bacterial cultures were used instead of the test formulation. The antibacterial activity was calculated by determining the difference in $\log_{10}$ colony-forming units (cfu) between control (Phosphate buffer saline) and test samples (i.e., $\log_{10}$ reduction). 3 experiments, each containing triplicate samples in each group, were performed. For comparison, triclosan and PCMX containing soap, and an alcohol (62%) hand sanitizer, were tested similarly at the same time.

TABLE 1

Rapid and broad antimicrobial efficacy of an aqueous botanical hand disinfectant foam and Purell by the FDA TFM method*

| | % kill | |
|---|---|---|
| Organism | Purell (62% Ethyl Alcohol) | Aqueous Botanical band disinfectant foam |
| S. aureus ATCC# 6538 | >99.99 | >99.99 |
| P. aeruginosa ATCC#15442 | >99.99 | >99.9 |
| E. coli ATCC#35218 | >99.999 | >99.999 |
| MRSA ATCC#4716 | >99.99 | >99.9 |
| S. epidermidis ATCC# 35983 | ND | 99.9 |
| E. faecalis ATCC# 29212 | ND | >99.9 |
| VREF Clinical isolate | ND | 99.9 |
| S. marcescens ATCC# 14756 | ND | >99.999 |
| A. baumanni Clinical isolate | ND | 99.9 |
| E. aerogenes ATCC#14053 | ND | >99.999 |
| K. pneumonia ATCC# 13883 | >99.99 | >99.999 |
| S. typhimurium ATCC#14028 | ND | >99.999 |
| C. albicans ATCC#10231 | ND | >99.999 |

ND = Not done

*FDA TFM = Tentative Final Monograph; ATCC = American Type Culture Collection; MRSA = Methicillin-resistant S. aureus; VREF = Vancomycin-resistant E. faecalis. The control growth ranged from $5 \times 10^8$ to $1 \times 10^9$ cfu/ml. Results are the average of twelve samples in each group.

Example 2

Rapid and Persistent Antibacterial Efficacy of an Aqueous Botanical Hand Disinfectant Foam A A pigskin test method was used to examine the antimicrobial efficacy of an aqueous botanical hand disinfectant. The pigskin test simulates the Volunteer method of the American Society for Testing and Materials (ASTM) E-1174 (Test organism: S. aureus). The hand foam tested comprised the following formulation.

| Aqueous Botanical Hand Disinfectant Foam A | |
|---|---|
| Ingredients | % w/w |
| Water | 78.15 |
| Hydroxypropyl methyl-cellulose stearoxy ether (Sangelose) | 0.1 |
| Allantoin | 0.3 |
| Grapefruit seed extract | 0.5 |
| Solubulizer (Peg-40 hydrogenated Castor oil, Trideceth 9, water) | 2.0 |
| SDA-40 B (natural) | 10 |
| Benzyl alcohol | 1.0 |
| Pentylene glycol | 1.0 |
| Phenoxyethanol | 1.0 |
| Aloe leaf juice | 0.5 |
| Bisabolol | 0.05 |
| Wasabi extract | 0.3 |
| Honeysuckle extract | 0.3 |
| Linalool | 0.1 |
| Lemongrass oil | 0.2 |
| Thymol | 0.1 |
| Phospholipid PTM (Croda) | 0.5 |
| Farnesol/Bisabolol | 0.5 |
| Cationic surfactant | 0.5 |
| Benzoic acid | 0.2 |
| Glucopon | 1.3 |
| Silicone (silsurf) | 1.4 |
| Adjust pH = 4.0-4.5 | |

Method:

3 cm² pieces of pigskins were prepared and each piece was mounted on a petri dish. For the baseline count determinations, 2 skin samples were rinsed under running tap water for 30 seconds and then lathered using 0.5 ml of non-antibacterial soap by rubbing both pieces together for 30 seconds. The pair was then rinsed under running tap water for 30 seconds and blot dried. Each piece of pigskin was contaminated with 15 µl of $10^7$ cfu/ml S. aureus culture and rubbed against each other for 30 seconds and dried for 30 seconds. The organisms were recovered from the skin by rinsing each piece with 10 ml of DNF for 15 seconds and collecting the wash. Aliquots from serial dilutions were uniformly spread on TSA plates, incubated for 24-48 hours at 37° C. To evaluate the efficacy of the test sanitizers, the same skin pieces used for baseline count determinations were rinsed under running tap water, washed with non-antibacterial soap, and recontaminated. After the 30-second drying period, 0.5 ml of the test sanitizer was applied on the skin and lathered for 30 seconds. After rinsing, the bacteria were recovered as described above. The contamination and sanitizer applications were repeated an additional 9 times. The bacterial counts after 1 and 10 applications were determined and the difference in $\log_{10}$ colony-forming units (cfu) between the baseline and test samples were calculated ($\log_{10}$ reduction). The antimicrobial activity of the hand disinfectant foam is shown below in Table 2.

TABLE 2

Rapid and persistent antibacterial efficacy of hand disinfectant foam A after repeated applications by the pig skin method (test organisms S. aureus (ATCC 6538))

| Test Soap | $Log_{10}$ reduction from control growth, mean ± SD S. aureus |
|---|---|
| Alcohol hand sanitizer (Purell) | |
| After $1^{st}$ application | 1.8 ± 0.08 |
| After $10^{th}$ application | 1.9 ± 0.05 |
| Aqueous botanical hand disinfectant foam A | |
| After $1^{st}$ application | 2.6 ± 0.06 |
| After $10^{th}$ application | 3.0 ± 0.05 |

Control counts ranged from $1 \times 10^5$ to $5 \times 10^5$ cfu/ml. Results are the average of twelve samples in each group.
Conclusion: As per US FDA-TFM criteria, the required $log_{10}$ reduction from control counts is 2.0 log after a first application for rapid antimicrobial activity, and 3.0 log after tenth application for persistent antimicrobial activity. Unlike the alcohol sanitizer Purell, an aqueous botanical hand disinfectant foam of the present subject matter exhibits the required US FDA-TFM criteria log reduction.

Example 3

Evaluation of the Antimicrobial Efficacy of a Surface Disinfectant: In Vitro Rapid Kill (15 Seconds) of S. aureus Method:

Surfactant (0.8 ml) was placed in a sterile culture tube and 0.2 ml of $10^9$ cfu/ml of test bacterial culture diluted 1:1 with bovine adult serum was added and mixed. After 15 s, the antimicrobial activity was stopped with drug neutralizing fluid (DNF). Serial dilutions were made with DNF and aliquots were subcultured on trypticase soy agar to determine the number of microbial colonies per sample. For controls, phosphate buffered saline (PBS) containing the same bacterial cultures was used instead of the test formulation. The antibacterial activity was calculated by determining the difference in $log_{10}$ colony-forming units (cfu) between control (phosphate buffer saline) and test samples (i.e., $log_{10}$ reduction). The surface disinfectant tested comprised the following formulation.

| Botanical Surface Disinfectant LG-50 | |
|---|---|
| Ingredients | % w/w |
| Lemongrass oil | 2.5 |
| Pine oil | 0.5 |
| Glucopon 215 UP | 25 |
| Citric acid | 10 |
| SDA 3C | 35 |
| Water | 27 |

The antimicrobial activity of the surface disinfectant is shown below in Table 3.

TABLE 3

| Compositions | Log reduction from control growth | % kill |
|---|---|---|
| Surface disinfectant LG-50 | 7.0 | 100 |
| Proquart (Clorox) * (1 oz diluted to 1 Gallon) | 3.85 | 99.95 |

TABLE 3-continued

| Compositions | Log reduction from control growth | % kill |
|---|---|---|
| Proquart (Clorox)* (2 oz diluted to 1 Gallon) | 4.26 | 99.99 |

*These contain long chain quaternary ammonium compounds

Control bacterial counts: 8.5-9.9 $log_{10}$

Dilutions of Proquart were made as described in the instructions on the product label: Proquart 0.17% quaternary ammonium compound (1 oz. and 2 oz.) was diluted to 1 gallon.

Conclusion. The botanical surface disinfectant showed higher antimicrobial efficacy than Proquart.

Example 4

Efficacy of Disinfectants on Bacteria Dried on Ceramic Tiles Following a 10 Minute Exposure to Compositions of the Application Method:

In this experiment, S. aureus, MRSA and E, coil were used as the test organisms. Ceramic tiles with dimensions of 5×15 $cm^2$ were cleaned first with water and then with 70% ethanol and dried. Approximately 0.1 ml of $1 \times 10^7$ cfu/ml of each microorganism was spread evenly on the surfaces of the tiles using a sterile glass rod, and allowed to dry for 1 hour. 0.3 ml of surface cleanser of the present subject matter was spread onto the tiles and allowed to dry at room temperature for 10 minutes. The tile surface was rinsed using 9.7 ml of Drug neutralizing fluid (DNF) into a sterile Petri dish to recover the remaining microorganisms on the tile. The recovered media was serially diluted, plated on TSA plates, and incubated at 37° C. for 18-24 hrs after which time colony counts were determined. For control, the same procedure was followed, except 0.3 ml of phosphate buffered saline was used instead of surface cleanser. Proquart, a commercial disinfectant containing quaternary ammonium compounds (10.85% quaternary ammonium compounds), from Clorox company was also evaluated simultaneously for comparison. The surface disinfectant tested comprised the following formulation.

| Botanical Surface Disinfectant LG-50 | |
| --- | --- |
| Ingredients | % w/w |
| Lemongrass oil | 2.5 |
| Pine oil | 0.5 |
| Glucopon 215 UP | 25 |
| Citric acid | 10 |
| SDA 3C | 35 |
| Water | 27 |

The antimicrobial activity of the surface disinfectant is shown below in Table 4.

TABLE 4

Efficacy of a 10 minute application of LG-50 surfactants on bacteria dried on ceramic tiles

| Composition | S. aureus | % kill MRSA | E. coli |
| --- | --- | --- | --- |
| Surface disinfectant LG-50 (1 oz diluted to 5 oz) | 99.999 | 99.99 | 99.9 |
| Proquart (1 oz diluted to 1 Gallon) | 99.0 | 99.0 | 99.0 |
| Proquart (2 oz diluted to 1 Gallon) | 99.9 | 99.9 | 99.0 |

Control growth ranged from $5 \times 10^5$-$1 \times 10^6$.
Dilutions of Proquart were made as described in the instructions on the product label: Proquart 0.17% quaternary ammonium compound (1 oz. and 2 oz.) was diluted to 1 gallon.
LG 50 comprising 0.12% essential oils (1 oz) was diluted to 5 oz.
Conclusion. The botanical surface disinfectant showed higher antimicrobial efficacy than Proquart.

Various patent and non-patent publications are cited herein, the contents of which are hereby incorporated by reference in their entireties.

We claim:

1. An antimicrobial composition comprising:
   (a) from about 0.5% (w/w) to about 2.0% (w/w) benzyl alcohol;
   (b) from about 0.05% (w/w) to about 1% (w/w) thymol; and
   (c) from about 0.5% (w/w) to about 10% (w/w) botanical extract selected from the group consisting of lemon extract.

2. The antimicrobial composition of claim 1, which further comprises phenoxyethanol.

* * * * *